United States Patent
Rucker

(10) Patent No.: US 10,173,018 B1
(45) Date of Patent: Jan. 8, 2019

(54) TAMPER RESISTANT CLAMP

(71) Applicant: Hal Rucker, Hillsborough, CA (US)

(72) Inventor: Hal Rucker, Hillsborough, CA (US)

( * ) Notice: Subject to any disclaimer, the term of this patent is extended or adjusted under 35 U.S.C. 154(b) by 540 days.

(21) Appl. No.: 14/840,280

(22) Filed: Aug. 31, 2015

Related U.S. Application Data

(60) Provisional application No. 62/068,913, filed on Oct. 27, 2014, provisional application No. 62/044,574, filed on Sep. 2, 2014.

(51) Int. Cl.
*A61M 5/50* (2006.01)
*A61M 25/02* (2006.01)

(52) U.S. Cl.
CPC ............ *A61M 5/5086* (2013.01); *A61M 5/50* (2013.01); *A61M 25/02* (2013.01); *A61M 2025/024* (2013.01)

(58) Field of Classification Search
CPC ............ A61M 39/1011; A61M 1/3653; A61M 2039/1027; A61M 2039/1077; A61M 39/162; A61M 5/5086; A61M 5/50; A61M 25/02; A61M 2025/024; Y10S 604/905

See application file for complete search history.

(56) References Cited

U.S. PATENT DOCUMENTS 4,631,056 A * 12/1986 Dye .................. A61M 39/1011
                                                            285/3
2014/0303595 A1   10/2014 Justus et al.

* cited by examiner

*Primary Examiner* — Brandy S Lee
(74) *Attorney, Agent, or Firm* — Patent Law Offices of Michael E. Woods; Michael E. Woods

(57) ABSTRACT

A system and method for deterring potential illicit use of extended-installations of catheters associated with patient care. A pair of legs are moveably associated together to collectively define a needle-defeating pathway between a pair of scissoring, offset, pinching surfaces disposed on mating surfaces of the legs when the legs are closed and clamped to an indwelling catheter. A single-use tamper evident locking system both maintains the legs closed and provides tamper evidence when opened, such as by disabling the locking system from further locking operation.

8 Claims, 24 Drawing Sheets

TAMPER RESISTANT CLAMP

CROSS REFERENCE TO RELATED APPLICATIONS

This application claims benefit of U.S. Patent Application No. 62/044,574 filed 2 Sep. 2014 and also claims benefit of U.S. Patent Application No. 62/068,913 filed 27 Oct. 2014, the contents in their entireties are hereby expressly incorporated by reference thereto for all purposes.

FIELD OF THE INVENTION

The present invention relates generally to access catheters, and more specifically, but not exclusively, to tamper resistant/evident clamps used in cooperation with extended installations of intravenous access catheters.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Treatment of chronic medical conditions such as infection, vasculitis, renal failure or cancer often requires that patients have intravenous access catheters inserted to administer medications, infusions, fluids, and the like (herein, collectively, the term "infusion" includes these cases. (Intravenous means inside a vein.) These hollow tubes or catheters are often quite long; some reach nearly to the heart. They come in a variety of lengths and styles. However, their purpose is generally similar: to administer fluids, medications, or nutrition into the large veins of the body over a prolonged period of time.

These catheters can remain in place for weeks or months. The advantages of these devices include: (1) high volumes of fluid may be administered into large central veins; (2) they may remain in place between giving the infusions, therefore obviating the need for frequent line changes; and (3) they often allow the patient to be discharged from the hospital to home or an alternate care facility (e.g., nursing facility and the like) which makes for less costly and more convenient care.

Although physicians often discharge patients out of the hospital with a central catheter in place, they or their staffs sometimes worry that persons with a history of administering illicit medications into their veins (intravenous drug abusers) will use the catheters to give themselves narcotics or other drugs. This could cause infection of the line. In addition, administration of a high dose of the illicit drug directly into a central vein could cause overdose and possibly death. Therefore hospitals often keep these patients in the hospital for weeks past the time when they could be discharged to home just to prevent abuse of the catheter. The catheters are not locked and therefore could be used for injection by the patients when they are at home not being observed. Prolonged hospital stays to deter potential abuse of installed catheters dramatically increase the costs of providing care and take up limited resources. Some patients may attempt to introduce unauthorized substances into these devices whether discharged or not.

What is needed is a mechanism for deterring potential illicit use of extended-installations of catheters associated with patient care.

BRIEF SUMMARY OF THE INVENTION

Disclosed is a system and method for deterring potential illicit use of extended-installations of catheters associated with patient care, whether discharged for outpatient treatment or still admitted to a care facility. The following summary of the invention is provided to facilitate an understanding of some of the technical features related to tamper-resistant/tamper-evident clamps used for central venous catheters, and is not intended to be a full description of the present invention. A full appreciation of the various aspects of the invention can be gained by taking the entire specification, claims, drawings, and abstract as a whole. The present invention is applicable to other flexible tubular channels in addition to catheters in situations where tamper-resistance/tamper-evidence is useful or necessary, and adaptions of the mechanism may be applied to provide tamper-resistance and tamper-evidence for a range of applications in addition to catheter access and control.

A purpose of the illustrated embodiments of the invention is to lock one or more catheter line and prevent their use between administrations of the medically indicated infusions. The device must close off the line and prevent its use between administrations of the required medications. It must be removable and tamper resistant or, at least, tamper evident. It must not damage the catheter and should be able to close off more than one line at a time to prevent the patient from accessing the line for purposes other than the intended medical use.

An embodiment of the present invention includes a hinged clamp, two independent pinching surfaces, two lateral walls and a linear ratchet mechanism. The hinged clamp can be produced as two separate pieces held together with a "pin" or "rivet" that serves as an axis of rotation for the pieces, or as one piece with a molded "living hinge". In either case, the hinge cannot be removed without destroying the unit. The two pinching surfaces rise from opposing planes such that a syringe needle cannot pass through the device when it is in the clamped mode, as further described herein. The two lateral walls interfere with a user's ability to slide the catheters off of the two pinching surfaces without destroying the device or the catheters.

A locking system, (e.g., a linear ratchet mechanism) holds the clamp closed in a position that prevents the passage of the syringe needle through the catheter such that the user cannot inject materials into the central channel of the catheter while the clamp is in the clamped position. When the device is opened after engagement of the locking system, the pawl of the ratchet mechanism or the hook that interfaces with the pawl breaks off in such a way that the clamp will no longer stay closed. Therefore, after the clamp has been closed and then opened, the locking mechanism is disabled and is unable to retain the clamp in the clamped mode.

An alternate embodiment of the present invention includes a clamp having three components, each of which has an option of being easily manufactured with common manufacturing techniques or additive manufacturing, e.g., three-dimensional printing systems. This alternate embodiment may include a bottom arm, a top arm, and a rotating knob disposed within an aperture of the top arm. A closure system, such as a catheter cradle or other generic closure system, is disposed on intermediate inside facing surfaces of the arms. The arms are preferably pivotally coupled to each other and rotate between an open and closed position. The arms may only be detached when they are in the opened mode. The bottom arm includes a bottom latching element at one end. The knob includes a complementary latching element that engages the bottom latching element when the arms are closed. This latching mechanism is designed to be permanent in the sense that it may not be unlatched without destruction of the latching system. For example, one or both of the latching elements may tear away from their attachment which enables the latching system to be delatched. The arms are designed so that they may be opened, after closure and engagement of the latching system, by destruction of the latching system. To facilitate and control the delatchment of the closed arms, the knob may be rotated. Rotation of the knob applies a shear force to components of the latching elements until they tear and separate. Stress risers are advantageously employed to focus the shearing forces to reliably and predictably tear away a latching element. Once delatched, the clamp may not be reclosed and relatched. Therefore a condition of the clamp in the opened and delatched state may indicate tampering or access of the system protected by the closure system.

An embodiment includes a clamp, having a first arm defining a first component of a closure system; a second arm, hingedly coupled to the first arm, defining a second component of the closure system, the second component of the closure system complementary to the first component, the closure system having an access enabled mode and an access inhibited mode wherein the components are engaged when the closure system is in the access inhibited mode and wherein the components are disengaged when the closure system is in the access enabled mode; and a single-use tamper-evident locking system coupled to the arms and configured to control the modes of the closure system, the closure system retained in the access inhibited mode when the legs are closed relative to each other and the single-use tamper-evident locking system is active to retain the arms in a closed mode wherein the single-use tamper-evident locking system is configured to destructively delatch before the arms may be operated to an opened mode after an engagement of the latching system wherein the closure system may be returned to an access enabled mode.

Another embodiment includes a tamper-evident clamping method, having the steps of a) rotating a first clamping arm relative to a second clamping arm about a pair of first ends of the arms, the arms defining a closure system on facing internal intermediate surfaces of the arms; b) closing the arms to engage the closure system producing a closed mode; and c) securing the arms together using a tamper-evident latching system coupled to a pair of second ends of the arms, the latching system configured to inhibit, after an actuation of the latching system, a delatchment of the latching system without a structural failure of the latching system to maintain the closure system in the closed mode until the arms are separated.

Embodiments of the invention may include two functions: (1) the clamp is tamper resistant—when clamped to a catheter, the clamp makes the catheter tamper resistant because it becomes very difficult, if at all possible, for a person to inject fluids into the central channel of the catheter when the clamp is clamped on the catheter; and (2) the clamp is tamper evident—if a patient defeats the tamper resistance by opening the closed clamp for any reason, the clamp becomes visibly and operationally damaged revealing the tampering when the clamp is next inspected.

Features of the disclosed embodiments include: (1) the hinge on the clamp cannot be removed without damaging the device, thus inhibiting the patient from disassembling the device to gain access to the catheter; (2) the two opposing pinching surfaces form a barrier that a straight syringe needle cannot pierce without destroying the device, thus interfering with or disabling a user from forcing a needle though the clamp to inject fluids into the catheter; (3) when the clamp is clamped and pinching off a catheter, two lateral walls on either side of the pinched catheter mate with a top leg of the closed clamp to create a barrier that prevents a user from sliding the catheter laterally off of the pinching surfaces to gain access to the catheter for injecting fluids; (4) one device may be used to clamp one or multiple catheters; and (5) the clamp works with catheters of different gauges within a range of diameters.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 9 illustrates a perspective view of the first alternate catheter clamp in a clamped mode;

FIG. 10 illustrates a perspective view of the first alternate catheter clamp in a pre-clamped mode;

FIG. 11 illustrates a detailed view of the paddle attached to a bottom arm using a set of break-away pins;

FIG. 12 illustrates a close-up detail of a pawl engagement to ratchet elements; and FIG. 13 illustrates a side-sectional view of the first alternate catheter clamp in the clamped mode.

FIG. 14 illustrates an exploded view of the second alternate catheter clamp;

FIG. 15 illustrates an isometric view of the second alternate catheter clamp in the closed mode;

FIG. 16 illustrates an isometric view of the second alternate catheter clamp in the open mode;

FIG. 17 illustrates a section view of the second alternate catheter clamp in the closed mode;

FIG. 18 illustrates a section view of the second alternate catheter clamp in the open mode;

FIG. 19 illustrates a side view of the second alternate catheter clamp in the closed mode;

FIG. 20 illustrates a side view of the second alternate catheter clamp in the open mode;

FIG. 21 illustrates a close-up detail of an attachment of the bottom hook to the bottom arm using posts having stress risers;

FIG. 22 illustrates the modified embodiment in the closed mode;

FIG. 23 illustrates the modified embodiment in the open mode; and

FIG. 24 illustrates a sectional view of the modified embodiment in the closed mode.

DETAILED DESCRIPTION OF THE INVENTION

Figure 1:
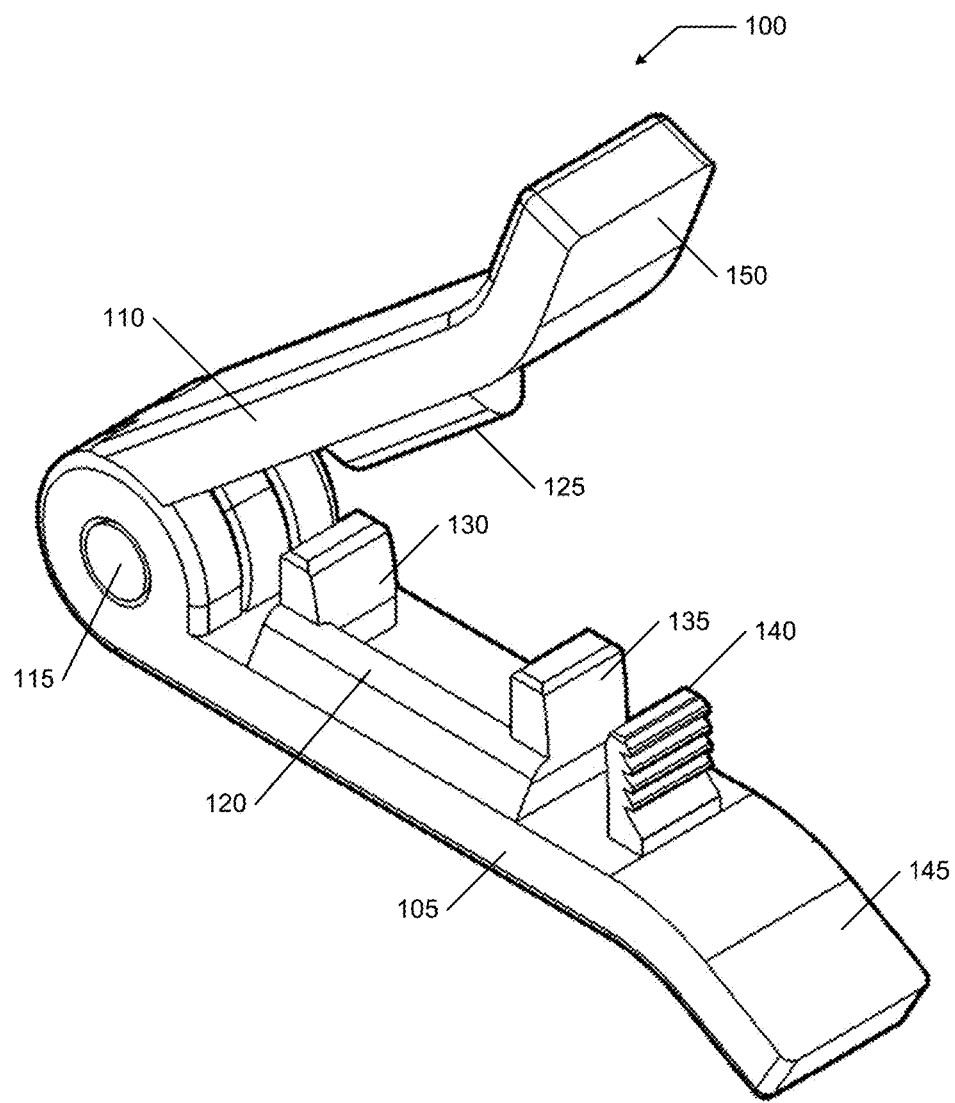
FIG. 1 illustrates a perspective view of a catheter clamp in a pre-clamped mode.

Embodiments of the present invention provide a system and method for deterring potential illicit use of extended-installations of catheters associated with patient care. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

As used herein, the term "catheter" refers to a thin, flexible tube or cannula extruded from medical grade materials inserted into a blood vessel, body cavity, duct, or other portion of a living body. The catheter includes an outer wall, flexible at least in a portion if not over most if not all of its length, and a central channel extending from one end to another end. For purposes of this disclosure, catheter is made of a material that allows at least the flexible portion to be collapsed or pinched off to close the central channel and prevent passage of a fluid (i.e., liquid or gas) past the collapsed portion.

As used herein, the term "indwelling catheter" refers to a catheter that is installed and is left in place, temporarily or permanently, under circumstances where the catheter may be accessed without proper supervision/control. For example, a catheter installed at a hospital and left in a discharged outpatient.

As used herein, the term "central venous catheter" refers to an indwelling catheter placed into a large vein in a neck (e.g., internal jugular vein), chest (e.g., subclavian or axillary vein), or groin (e.g., femoral vein).

As illustrated, the embodiment of the present invention functions properly with multiple catheters not necessarily of the same gauge or diameter size. That is, the embodiment functions properly with two or more catheters of differing gauges selected from within a range of gauges, e.g., gauge X to gauge Y. Another embodiment may function with a different range, for example, gauge X to gauge 3Y. As illustrated, the embodiment is designed to work with catheters sized 5 to 8 French, but other embodiments may operate with different sizes and different ranges.

Figure 2:
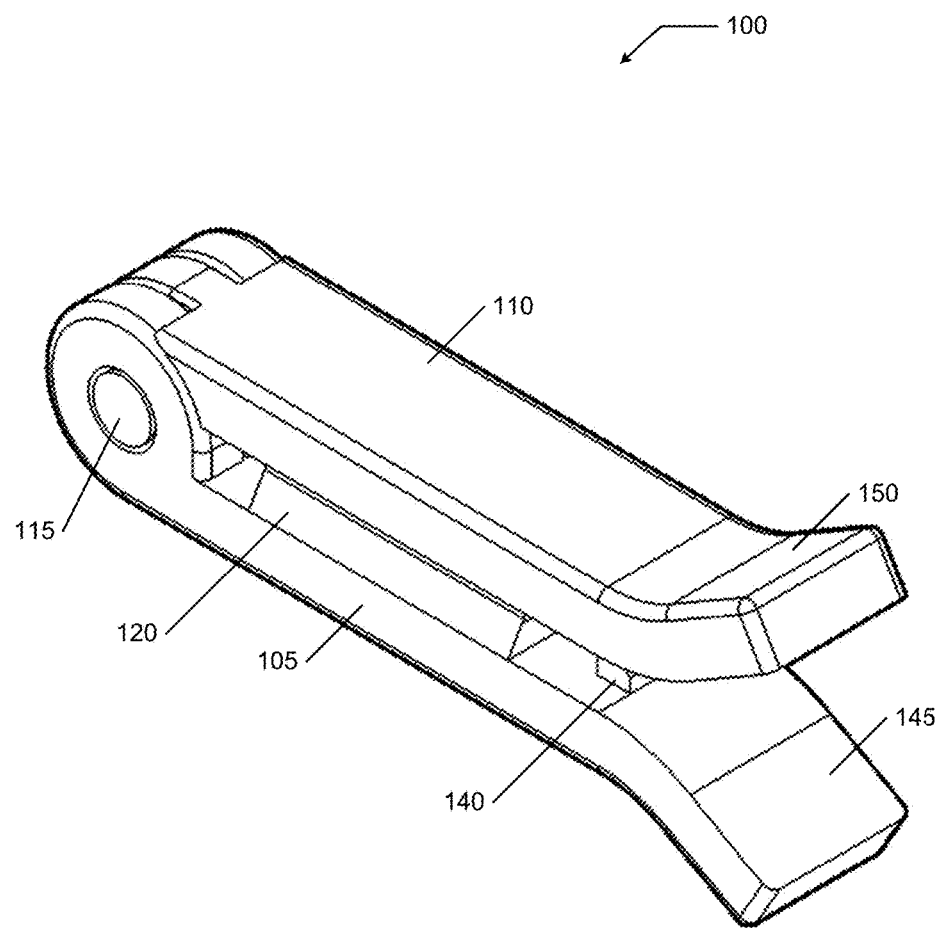
FIG. 2 illustrates a perspective view of the catheter clamp of FIG. 1, in a clamped mode.

FIG. 1 illustrates a perspective view of a catheter clamp 100 in a pre-clamped mode; and FIG. 2 illustrates a perspective view of catheter clamp 100 in a clamped mode. Clamp 100 includes a first leg 105 and a second leg 110. In the illustrated embodiment, a first end of second leg 110 is hingedly attached to a first end of first leg 105 using a pivot 115. The hinging arrangement in cooperation with the legs is configured so that the legs may not be detached without disabling an ability for the legs to be hingedly reattached. That is, once clamp 100 is assembled with second leg 110 is hingedly attached to first leg 105, detaching second leg 110 from first leg 105 makes hinged reattachment very difficult if at all possible. In some implementations, first leg 105 and second leg 110 are opposing portions of single body, these two portions joined by a "living hinge" connected to both legs.

First leg 105 includes a first pinching surface 120 disposed at one outside edge and second leg 110 includes a second pinching surface 125 disposed at another outside edge. First pinching surface 120 and second pinching surface 125 each extend longitudinally and are displaced about a longitudinal axis with respect to each other.

First leg 105 includes a first lateral wall 130 at a first end of first pinching surface 120 and a second lateral wall 135 at a second end of first pinching surface 120. The lateral walls are generally symmetric about the longitudinal axis. Free ends of the lateral walls extend sufficiently far from first leg 105 to enter within complementary matching cavities defined at a pair of ends of second pinching surface 125.

First leg 105 further includes a linear ratchet 140 that cooperates with a pawl (illustrated in FIG. 5 and FIG. 6) to produce a locking system for clamp 100. Ratchet 140 engages the pawl when clamp 100 is clamped in such a way that first leg 105 is held closed relative to second leg 110. The engagement of the components of the locking system permit one-way ratcheting to close and hold clamp 100 in the clamping mode. A top of linear ratchet 140 includes opposing sloped surfaces that help to guide a body of linear ratchet 140 into a corresponding receiving cavity as further explained herein.

A second end of first leg 105 includes a flared portion 145 and a second end of second leg 110 includes a flared portion 150. These flared portions help to transition clamp 100 between its modes. For example, as illustrated, the flared portions allow an operator sufficient space between flared portion 145 and flared portion 150 to fit ends of the operator's fingers and to thereby exert a force to separate the first leg 105 and second leg 110. In this implementation, the force required must be sufficient to defeat the one-way locking mechanism, such as, for example, tearing or otherwise detaching pawl 520 from within receiving cavity 515. Detaching pawl 520 allows the legs to be separated while preventing re-use of the locking mechanism to subsequently secure the legs in a subsequent clamped mode.

There are a variety of ways to make a hinge tamper-proof in the illustrated embodiment. For example, catheter clamp 100 includes a blind hole with a pin press fit into the blind hole. So the patient is unable to access the pin and poke it out from one side because there's a wall, and can't get to the pin to pull it out without destroying the device because it is pressed into the hole and recessed.

Figure 3:
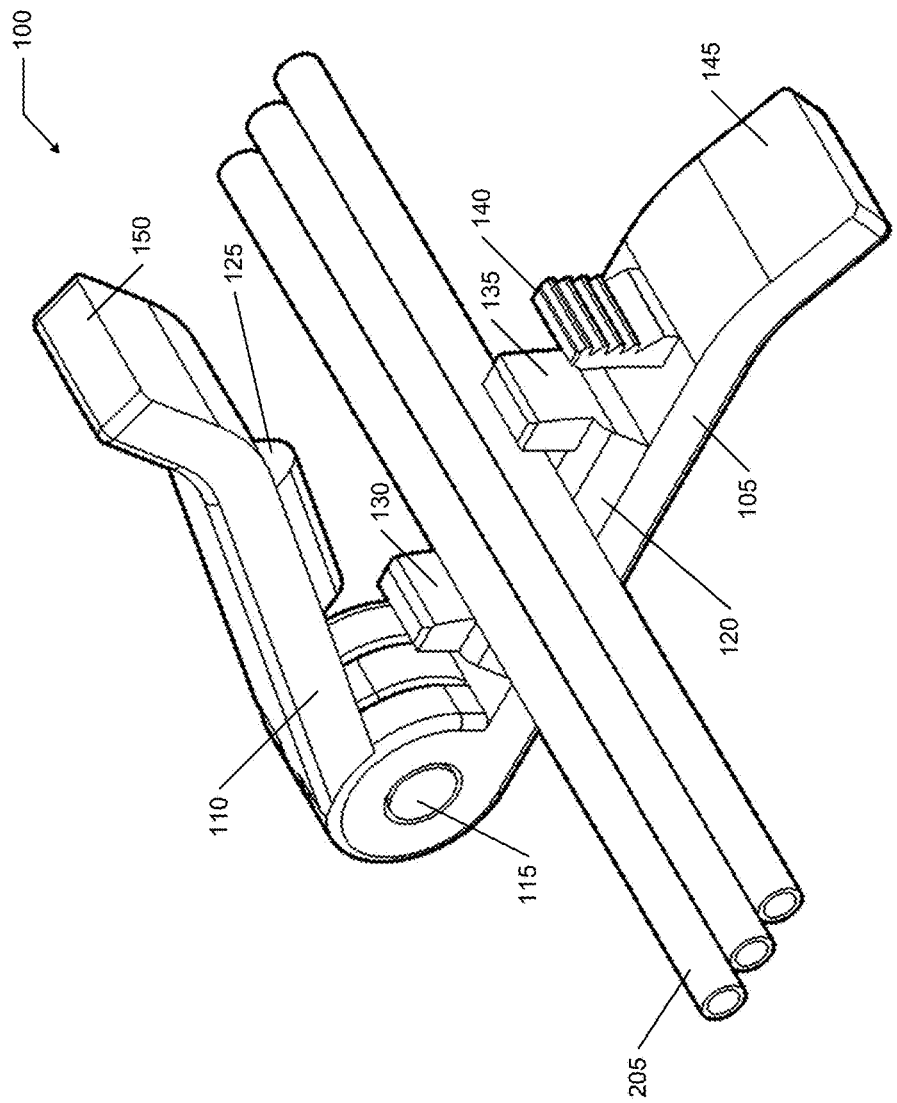
FIG. 3 illustrates a perspective view of the catheter of FIG. 1 including three indwelling catheters.
Figure 4:
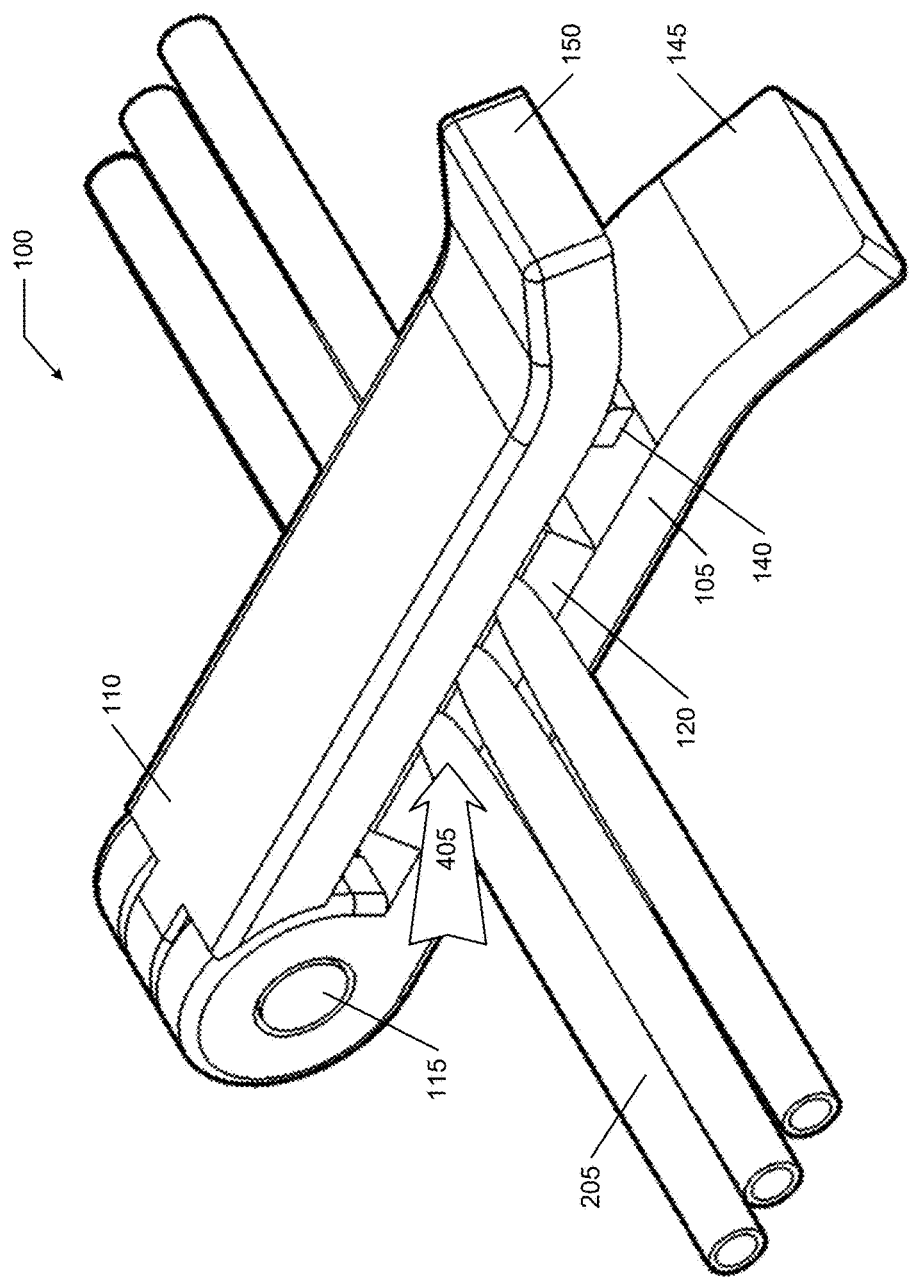
FIG. 4 illustrates a perspective view of the catheter of FIG. 3 transitioned to the clamped mode.

General operation of clamp 100 is illustrated in FIG. 3 and in FIG. 4 while more specific details of the structure and operation are illustrated in FIG. 5-FIG. 8. FIG. 3 illustrates a perspective view of catheter clamp 100 including portions of three indwelling catheters 205 and FIG. 4 illustrates a perspective view of the catheter of FIG. 3 transitioned to the clamped mode. Clamp 100 is illustrated as supporting up to three catheters 205, though other embodiments may be configured to accommodate a different number of catheters. Accommodation for differing numbers of catheters 205 is determined primarily by a longitudinal distance between first lateral wall 130 and second lateral wall 135.

Clamp 100 is configured to also accommodate differing gauges (diameters/thicknesses) of catheters 205. Gauge accommodation is determined primarily by a height of the pinching surfaces above their associated legs.

In practice, one end of each catheter 205 is free while an opposing end is installed within the body (not illustrated). An operator positions clamp 100 in the pre-clamped mode within a pocket "U-shaped" pocket formed by first pinching surface 120, first lateral wall 130, and second lateral wall 135. Clamp 100 may be located at a desired location by sliding clamp 100 closer towards (or further away) the one or more free ends of catheter(s) 205 while maintaining catheter(s) 205 within the pocket. In some embodiments, an arrangement of ratchet 140 and a gauge of catheter(s) 205 may enable clamp 100 to be partially closed while still permitting desired positioning.

While many catheters 205 have a fairly uniform construction along their length, with most portions including flexible walls that permit pinching/closing of the central channel, some catheters may not be so arranged. These catheters may have one or more selective portions that include flexible outer walls. Irrespective of which type of catheter 205 is installed, a flexible portion is positioned within the pocket.

After positioning clamp 100 at the desired location, clamp 100 is transitioned to the clamping mode by activating the locking system. In the clamping mode, second pinching surface 125 closes the "open" portion of the "U-shaped" pocket to capture and secure catheter(s) 205. As the legs of clamp 100 close, a scissoring action is formed between the laterally displaced pinching surfaces against the flexible portion of catheter(s) 205. This scissoring action does not sever catheter(s) 205, but does pinch, collapsed, and close the central channel within each catheter 205 to establish and maintain a pinched portion 405. The locking mechanism retains clamp 100 in the clamped mode which in turn maintains the engagement of the opposing pinching surfaces with catheter(s) 205 to close the central channels of each.

Figure 5:
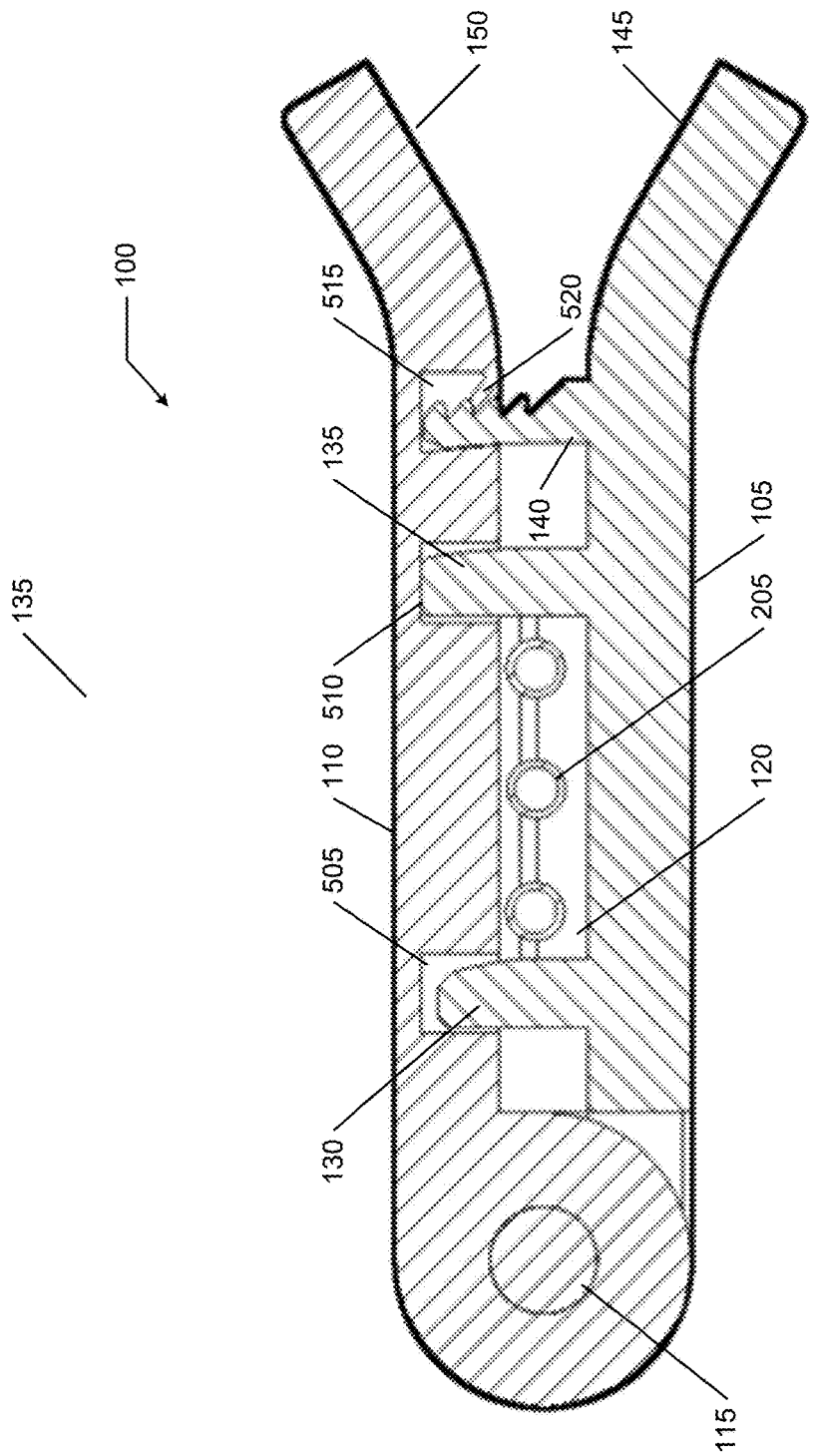
FIG. 5 illustrates a side sectional view of the catheter of FIG. 4.
Figure 6:
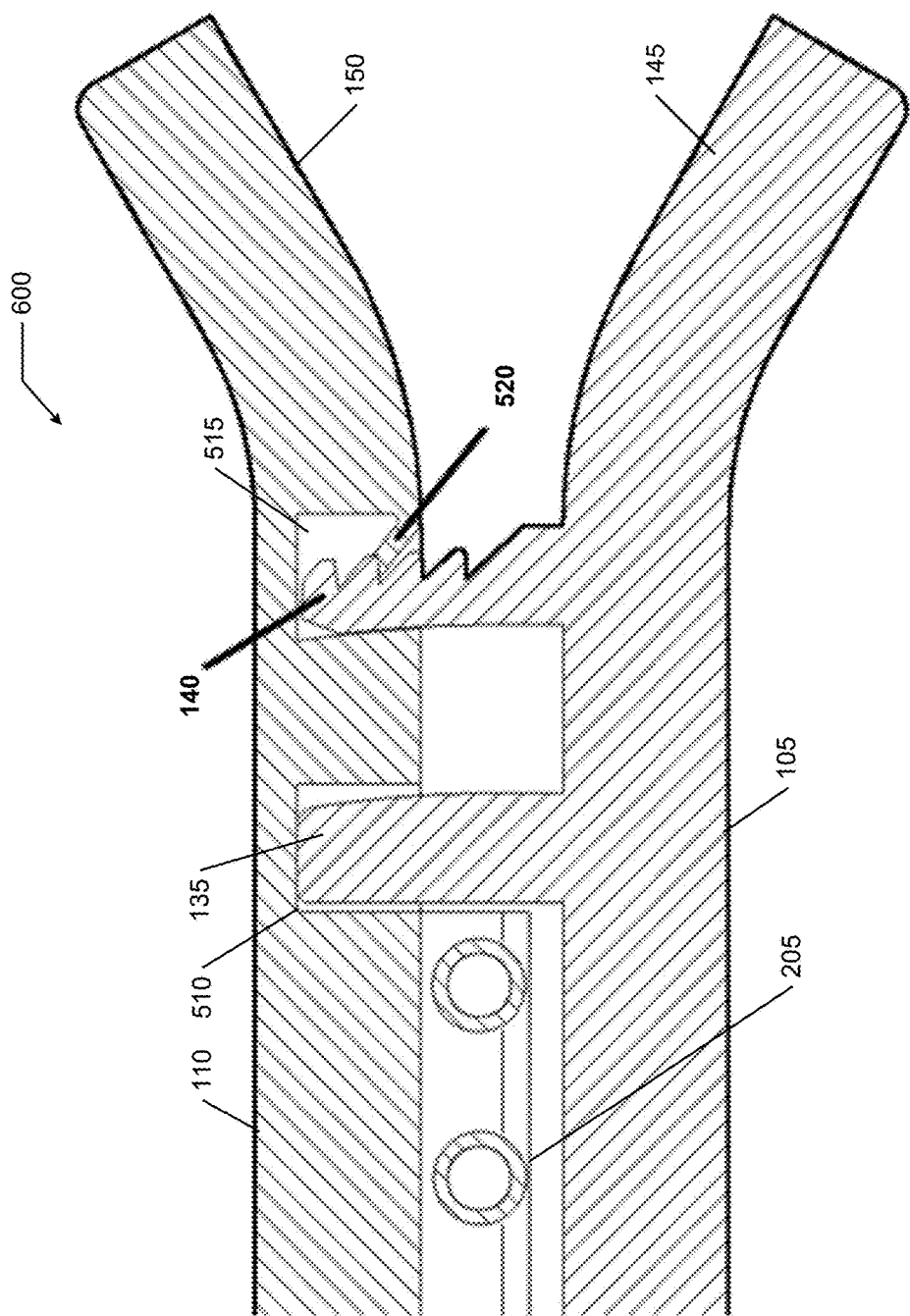
FIG. 6 illustrates an enlarged view of a portion of the side sectional view of FIG. 5.
Figure 7:
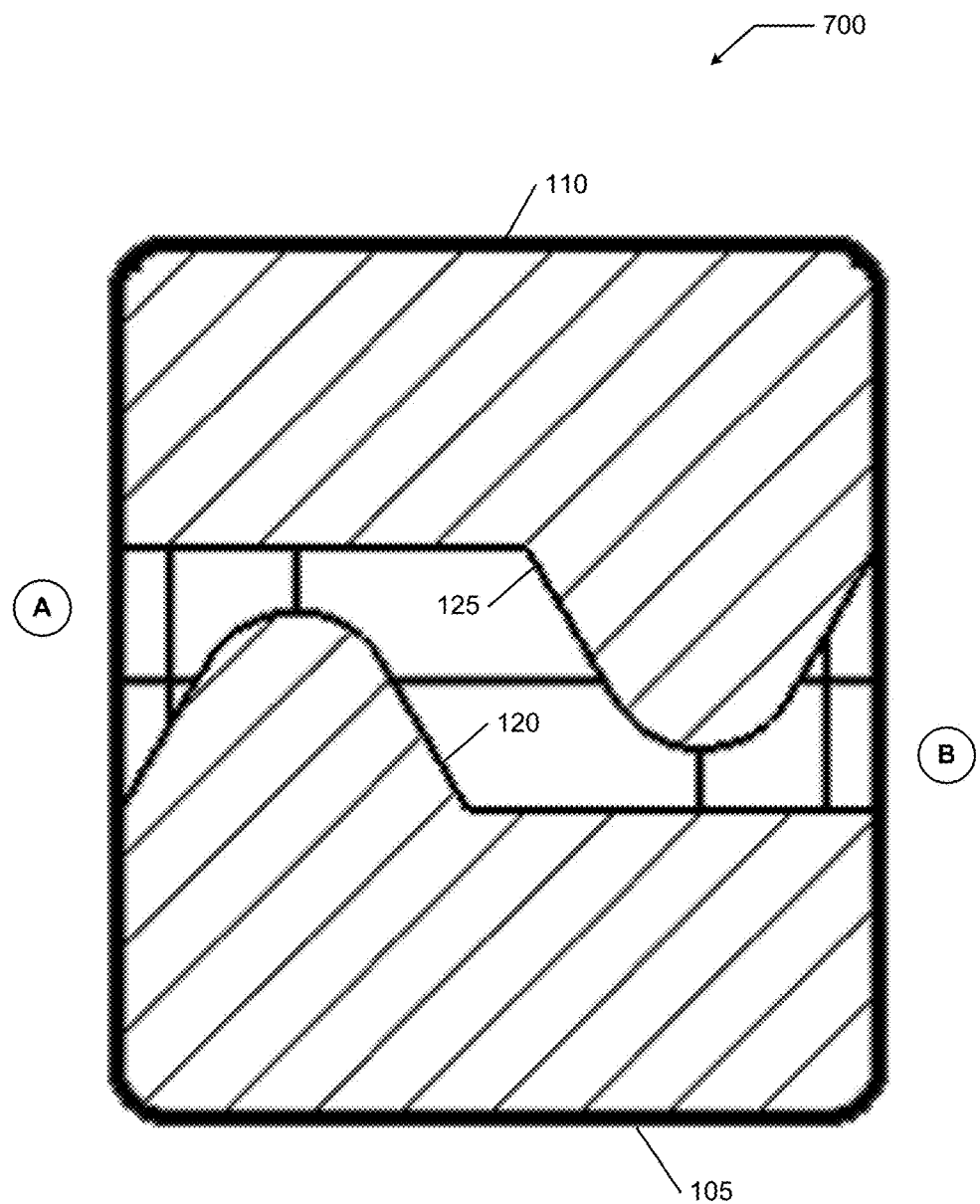
FIG. 7 illustrates a lateral sectional view of the catheter of FIG. 4 looking towards the hinged ends of the legs.

FIG. 5 illustrates a side sectional view of the catheter of FIG. 4; FIG. 6 illustrates an enlarged view of a portion 600 of the side sectional view of FIG. 5; and FIG. 7 illustrates a lateral sectional view 700 of the catheter of FIG. 4. Second leg 110 defines three receiving cavities: a first cavity 505 complementary and corresponding to first lateral wall 130, a second cavity 510 complementary and corresponding to second lateral wall 135, and a third cavity 515 complementary and corresponding to linear ratchet 140. A pawl 520 is disposed within third cavity 515 to ratchetedly engage a set of teeth disposed on a surface of linear ratchet 140. An arrangement and orientation of linear ratchet 140 and pawl 520 allow a one-way transition of clamp 100 from the pre-clamped mode to the clamped mode. Once clamped, a relative separation of first leg 105 and second leg 110 damages pawl 520 (e.g., torn away) to prevent or inhibit further transitions to the clamped mode.

As illustrated in FIG. 5, the free ends of the lateral walls disposed within the receiving cavities may be contoured to better allow free and unobstructed hinged relative rotation of the legs when transitioning to the clamped mode. In some embodiments, the teeth of linear ratchet 140 may face towards the first ends of the legs rather than facing towards the second ends as illustrated (with a corresponding relocation of pawl 520 within cavity 515.

The receiving cavities are illustrated as inaccessible except through a single cavity opening. This is particularly important in the illustrated embodiment with respect to receiving cavity 515 for linear ratchet 140. This is a detail that helps to make clamp 100 tamper-resistant as the closed receiving cavity 515 limits user access to pawl 520 (and/or linear ratchet 140 within cavity 515) and inhibits or prevents the user from using a small tool (e.g., a paperclip or the like) to release the locking mechanism and separate the legs.

Further, receiving cavity 515 is also ramped (gets smaller) such that the size of the opening gets smaller to: (1) guide linear ratchet 140 into cavity 515, and (2) locate and capture the top of linear ratchet 140 in the base of cavity 515 which is narrow, holds ratchet 140 between the two lateral walls, and makes it difficult to move the ratchet when it is disposed within cavity 515.

In FIG. 7, the lateral offset of first pinching surface 120 with respect to second pinching surface 125 is illustrated with clamp 100 in the clamping mode. Further, the relative height of these pinching surfaces is illustrated showing a non-aligned needle-defeating pathway from a point A on one side of clamp 100 to a point B on an opposing side of clamp 100 that extends past both pinching surfaces. This is the path that the pinched portions of catheters 205 take with clamp 100 in the clamped mode. (Note that point A and point B are positioned at different relative heights as compared to leg 105.)

Figure 8:
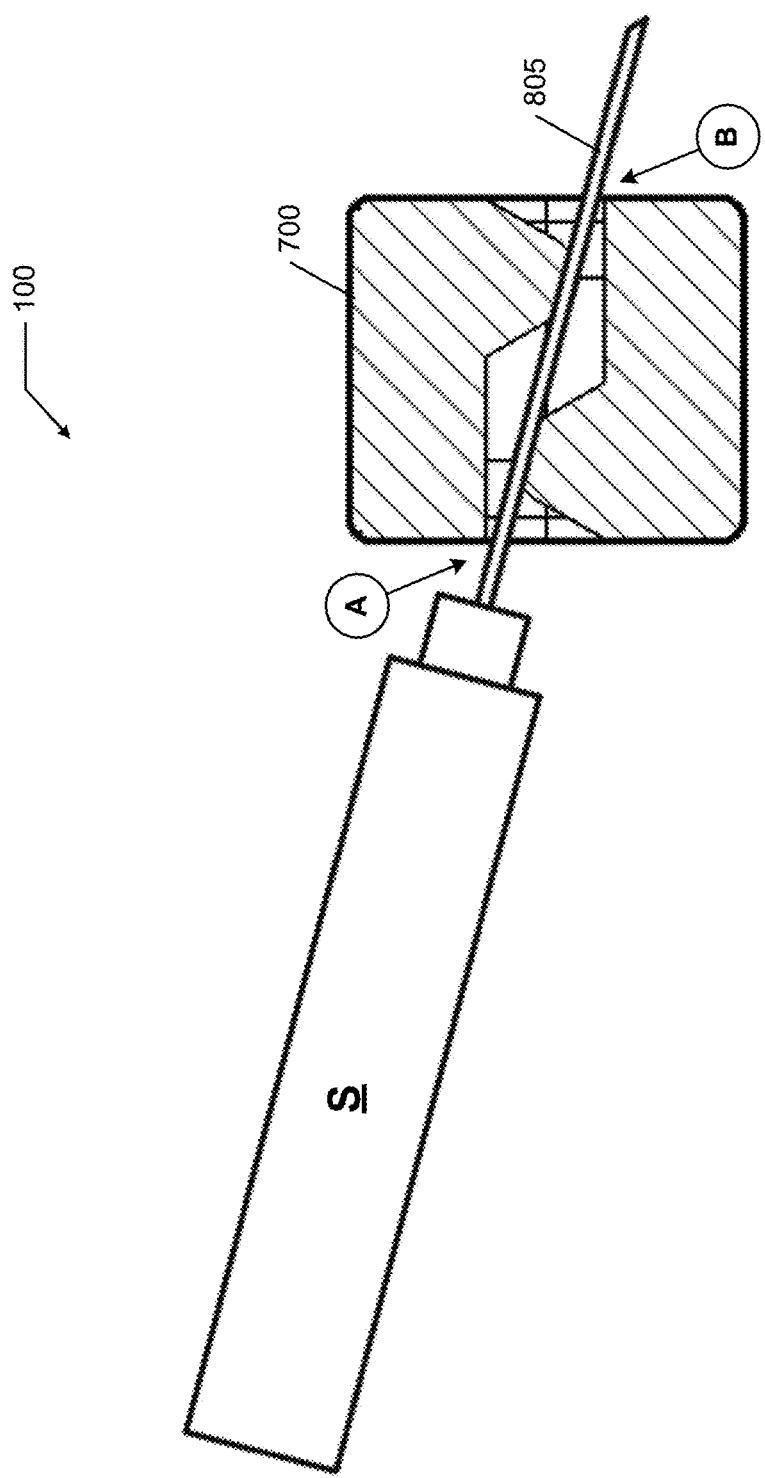
FIG. 8 illustrates a channel blockage inhibiting syringe access to a channel of the catheter of FIG. 4.

FIG. 8 illustrates a channel blockage inhibiting syringe access to a channel of the catheter of FIG. 4. A syringe S includes a needle 805 that is unable to follow the non-aligned needle-defeating pathway from point A to point B that the catheter does follow inside clamp 100 in the clamped mode. Needle 805 would not actually extend as shown as it would be intercepted by one or both pinching surfaces. A user would need to try and force needle 805 through one or both pinching surfaces which risks breaking needle 805 (resists tampering) or gouging one or both pinching surfaces (tamper evident).

In the preceding discussion, clamp 100 has been described as including two modes: a pre-clamped mode and a clamped mode. As illustrated and configured, clamp 100 transitions from the pre-clamped mode to the clamped mode but not from the clamped mode to the pre-clamped mode. Opening clamp 100 when clamped is designed to render clamp 100 unsuitable for additional clamping.

Alternate embodiments may include a pair of detached symmetric legs, each with a ratchet at one end and a recessed pawl at the other. Similarly, each leg includes one lateral wall at one end of a pinching surface and lateral-wall-receiving cavity at the other end of the pinching surface. In this embodiment, only a single leg configuration is needed without having a pivot or assembly step. In some situations this embodiment may be different to use in that the flexible wall portions of the catheters to be clamped are not laterally constrained on two sides when clamp 100 is closed.

In some variations of the embodiments of the present invention, the locking mechanism may be implemented to include a portion of the lateral side walls. For example, one or more of the lateral walls may further include ratchet teeth and the complementary associated receiving cavities may include engagement pawls. This may be in addition to or in lieu of ratchet 140 and pawl 520.

In some situations, the tamper evidence of catheter clamp 100 may not be as prominent as desired upon a visual inspection. Tamper evidence of catheter clamp 100 is 100% insofar as, once opened, it could not be re-used. Tamper evidence was established by attempting to clamp it shut from an unclamped mode. When the clamp would not remain closed, it was evidence of tampering. While effective for tamper evidence, it is less desirable for caregivers attempting to install an un-used clamp. When open, both a fresh catheter clamp and a used catheter clamp may appear the same, especially to a busy caregiver focusing on the patient. In some applications it may be preferable to provide an unused clamping catheter that is visually distinct from an opened previously clamped clamping catheter.

In some situations, the tamper evident feature of the locking mechanism of catheter clamp 100 may increase a concern about a risk of applying a sudden force to the clamped catheters when opening a clamped catheter clamp 100. As illustrated herein, the locking mechanism of catheter clamp 100 operates in the same plane as the opening and closing of the complementary arms. Thus, a caregiver could be concerned that there is an increased risk of applying a "tugging" force on the deployed catheters when trying to open a clamped catheter clamp 100. This concern may be due to a perception that pulling on the locked arms to separate them could result in the catheter arms suddenly opening and surprising the caregiver. This surprise may invoke a feeling of a lack of control of the locking mechanism and result in the caregiver fearing that a consequence of the lack of control may be an application of a removal force to the deployed catheters. In some applications it may be preferable to provide a controllable latching mechanism that helps relieve this concern of a caregiver, and, in the event that there may be some increased risk of injury to the patient, to reduce any risk associated with unlocking a clamped catheter.

FIG. 9-FIG. 13 illustrate a first alternate embodiment for a catheter clamp 900 that improves visual perception of a used catheter and offers an alternative latching mechanism that operates orthogonally to the opening/closing plane of the arms. Catheter clamp 900 incorporates the features and functions of catheter clamp 100 except with respect to the latching a tamper evident features. The closure system, that includes the pinching surfaces disposed between lateral walls, is common between catheter clamp 100 and catheter clamp 900.

Figure 9:
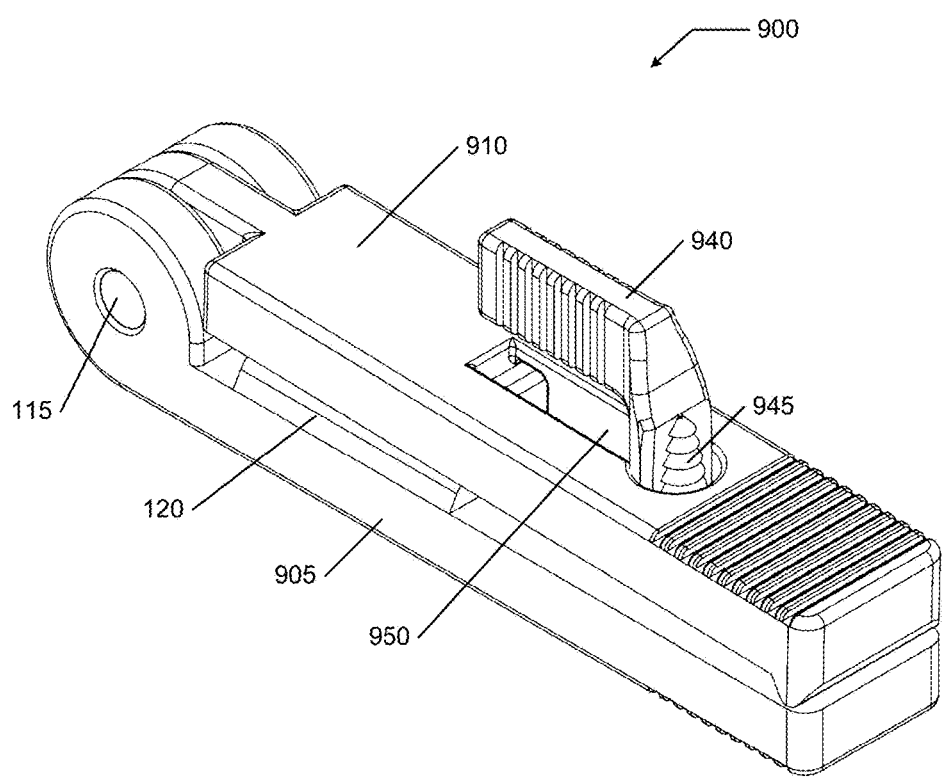
FIG. 9-FIG. 13 illustrate a first alternate embodiment for a catheter clamp.
Figure 10:
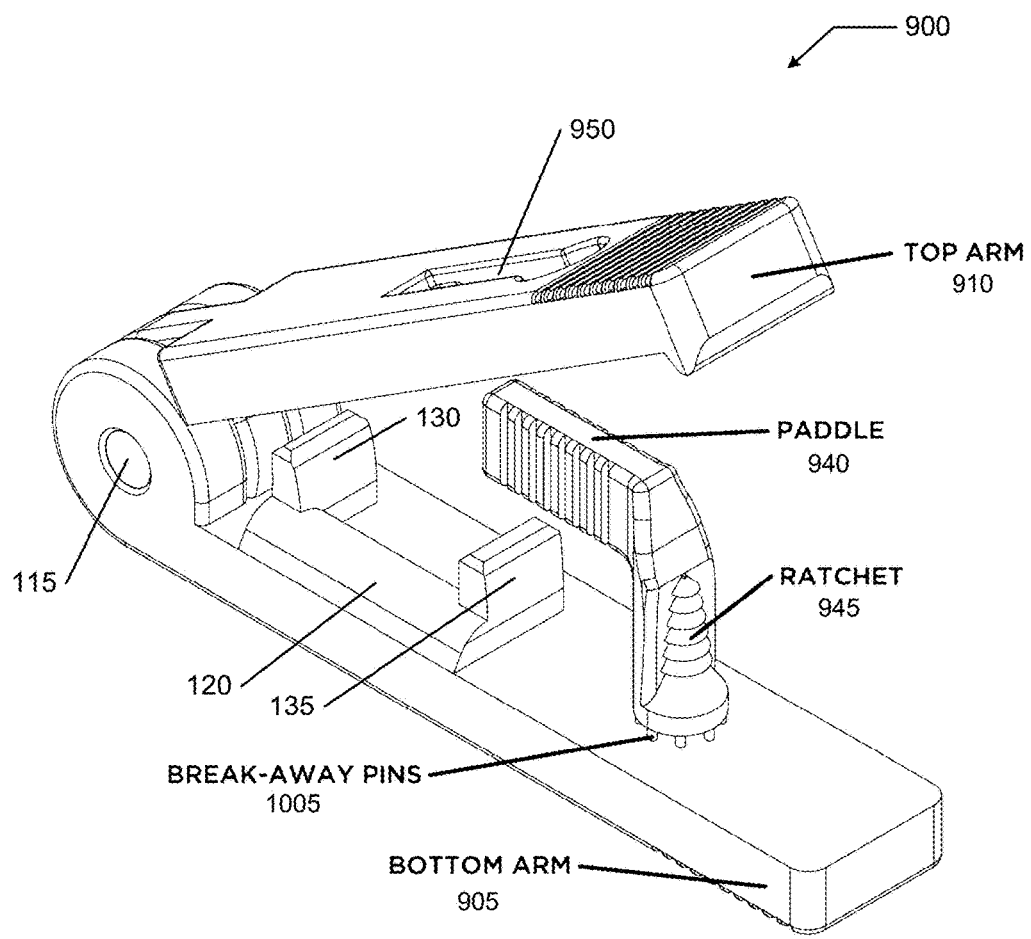

FIG. 9 illustrates a perspective view of catheter clamp 900 in a clamped mode; and FIG. 10 illustrates a perspective view of catheter clamp 900 in a pre-clamped mode. Clamp 900 includes a first leg 905 and a second leg 910. In the illustrated embodiment, a first end of second leg 910 is hingedly attached to a first end of first leg 905 using pivot 115. The hinging arrangement in cooperation with the legs is configured so that the legs may not be detached without disabling an ability for the legs to be hingedly reattached as described herein. In some implementations, first leg 905 and second leg 910 are opposing portions of single body, these two portions joined by a "living hinge" connected to both legs.

First leg 905 includes a first pinching surface 120 disposed at one outside edge and second leg 910 includes a second pinching surface 125 (not illustrated in FIG. 9-FIG. 13) disposed at another outside edge. First pinching surface 120 and second pinching surface 125 each extend longitudinally and are displaced about a longitudinal axis with respect to each other.

First leg 905 includes a first lateral wall 130 at a first end of first pinching surface 120 and a second lateral wall 135 at a second end of first pinching surface 120. The lateral walls are generally symmetric about the longitudinal axis. Free ends of the lateral walls extend sufficiently far from first leg 905 to enter within complementary matching cavities defined at a pair of ends of second pinching surface 125.

First leg 905 further includes a paddle 940 defining a ratchet surface 945 that cooperates with a pawl (illustrated in FIG. 12 and FIG. 13) to produce a modified locking system (as compared with the locking system of clamp 100, for example) for clamp 900. Second leg 910 includes a clearance hole 950 to allow passage of paddle 940 therethrough and also configured to precisely locate the pawl against ratchet surface 945.

Ratchet surface 945 engages the pawl when clamp 900 is clamped in such a way that first leg 905 is held closed relative to second leg 910. The engagement of the components of the locking system permit one-way ratcheting to close and hold clamp 900 in the clamping mode.

Paddle 940 is attached to first leg 905 using a destructive tear-away attachment mechanism, for example a set of break-away pins 1005. Paddle 940 includes a handle aligned with a longitudinal axis of the legs attached to a shaft extending perpendicularly from first leg 905. The handle is also aligned with rectilinear clearance hole 950. A twisting of paddle 940 by rotating the handle about the shaft tears, breaks, or otherwise defeats the attachment mechanism, allowing paddle 940 to be completely separated from leg 905. The modified locking mechanism requires that paddle 940 be attached to first leg 905, thus separation of paddle 940 from first leg 905 unlocks the modified locking mechanism and allows the pair of legs to be easily separated. The twisting of paddle 940 is in a different plane as compared to a plane containing the motion of the legs when opening and closing. Additionally, the twisting of paddle 940 is controllable and offers much less accidental opportunity to apply a removal force to any catheter clamped and locked by clamp 900.

The absence of the paddle is both a visual cue that clamp 900 has been opened and also an easily noticeable evidence of tampering in the event that the caregiver has not detached paddle 940.

Figure 11:
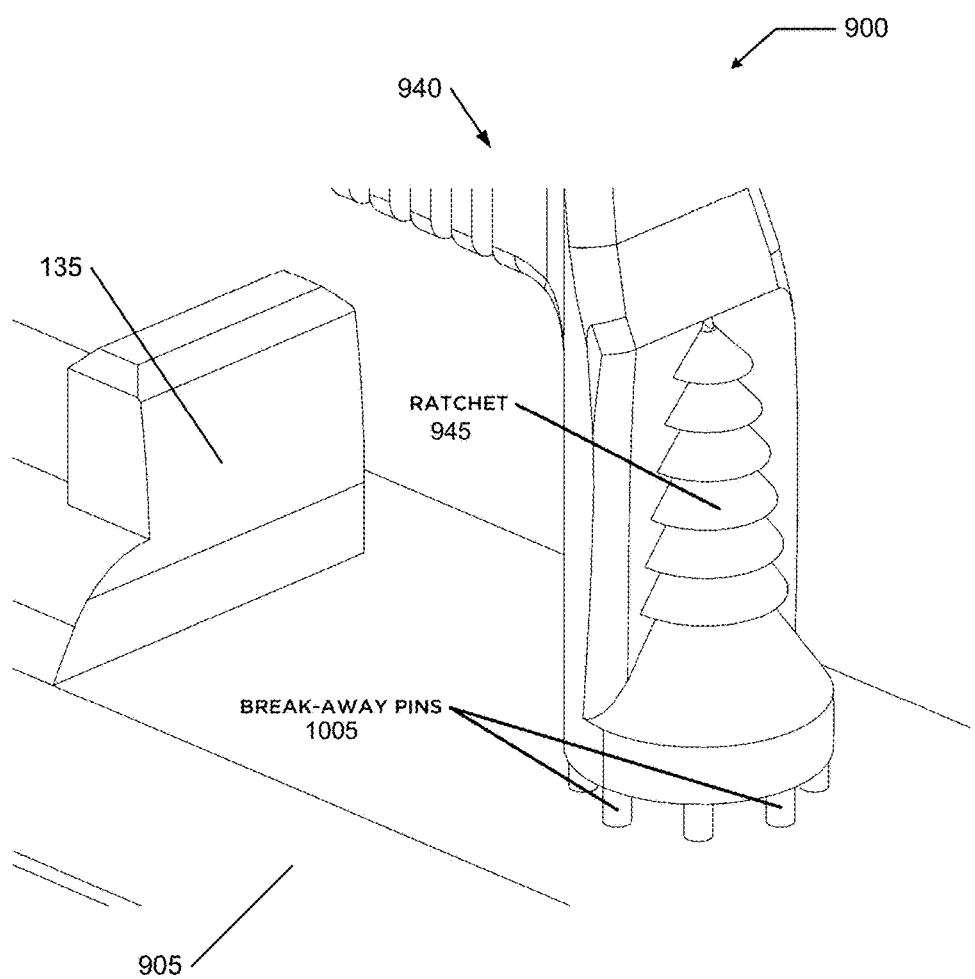
Figure 12:
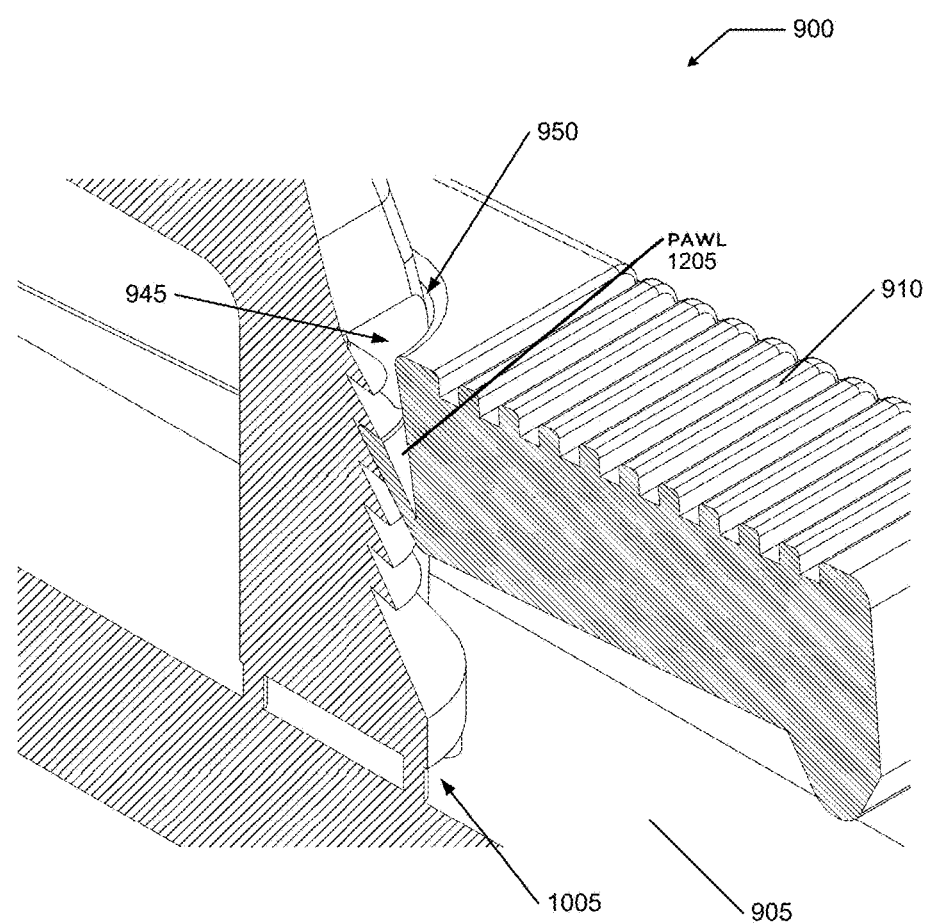
Figure 13:
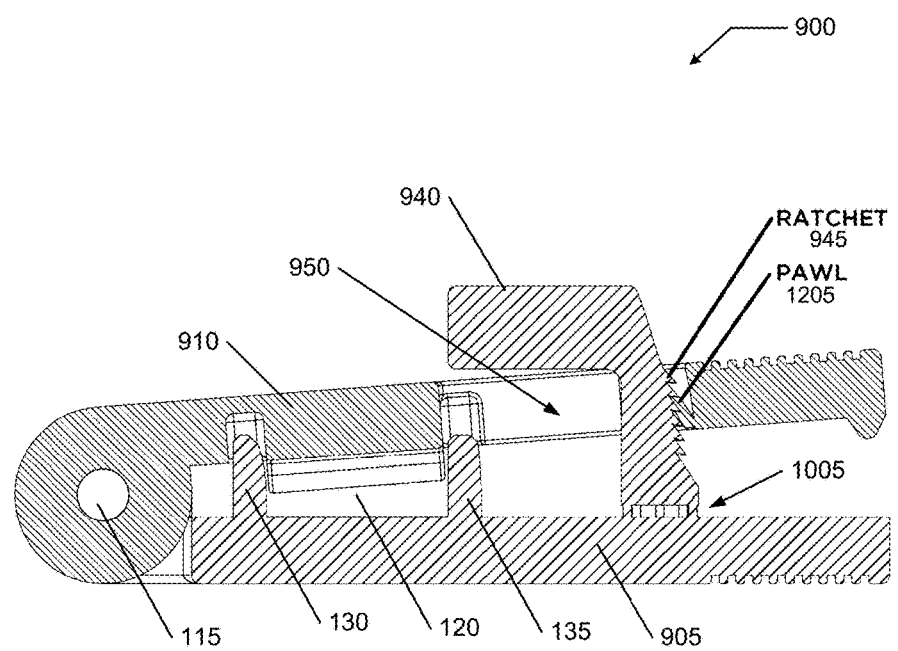

FIG. 11 illustrates a detailed view of paddle 940 attached to first leg 905 using a set of break-away pins 1005 as well as ratchet surface 945 defined in the shaft; FIG. 12 illustrates a close-up detail of a pawl engagement 1205 (defined in second leg 910 around an interior of clearance hole 950) to ratchet surface 945; and FIG. 13 illustrates a side-sectional view of catheter clamp 900 in the clamped mode.

The device is assembled in the open state. The caregiver places the catheter(s) on the rounded raised areas between the two containing lateral walls. When the caregiver closes the device, the pawl in the second leg interfaces with the ratchet surface on the paddle of the first leg in such a way that the device is locked and secured in the closed state, thus pinching the catheters closed as well. When an authorized caregiver wants to open and remove the device, the paddle is rotated, which breaks the small columns at the base of the paddle. At this point the caregiver can open the device, and the device cannot be locked in the clamped position again while visually indicating that the device has been previously used.

A unique feature of the device is the rotary ratchet and pawl mechanism. When the two legs are rotated to close the device, the pawl interfaces with the ratchet to lock it shut. The circular cross section of the paddle shaft locates tightly in the circular opening in the upper arm, thereby accurately controlling the positions of the ratchet and pawl relative to each other. Then, when the paddle is rotated to break the small columns at the base of the paddle, the rotary ratchet and pawl mechanism geometry allows the paddle to rotate within the circular cutout in the upper arm. A traditional linear ratchet would not allow the paddle to rotate.

Figure 14:
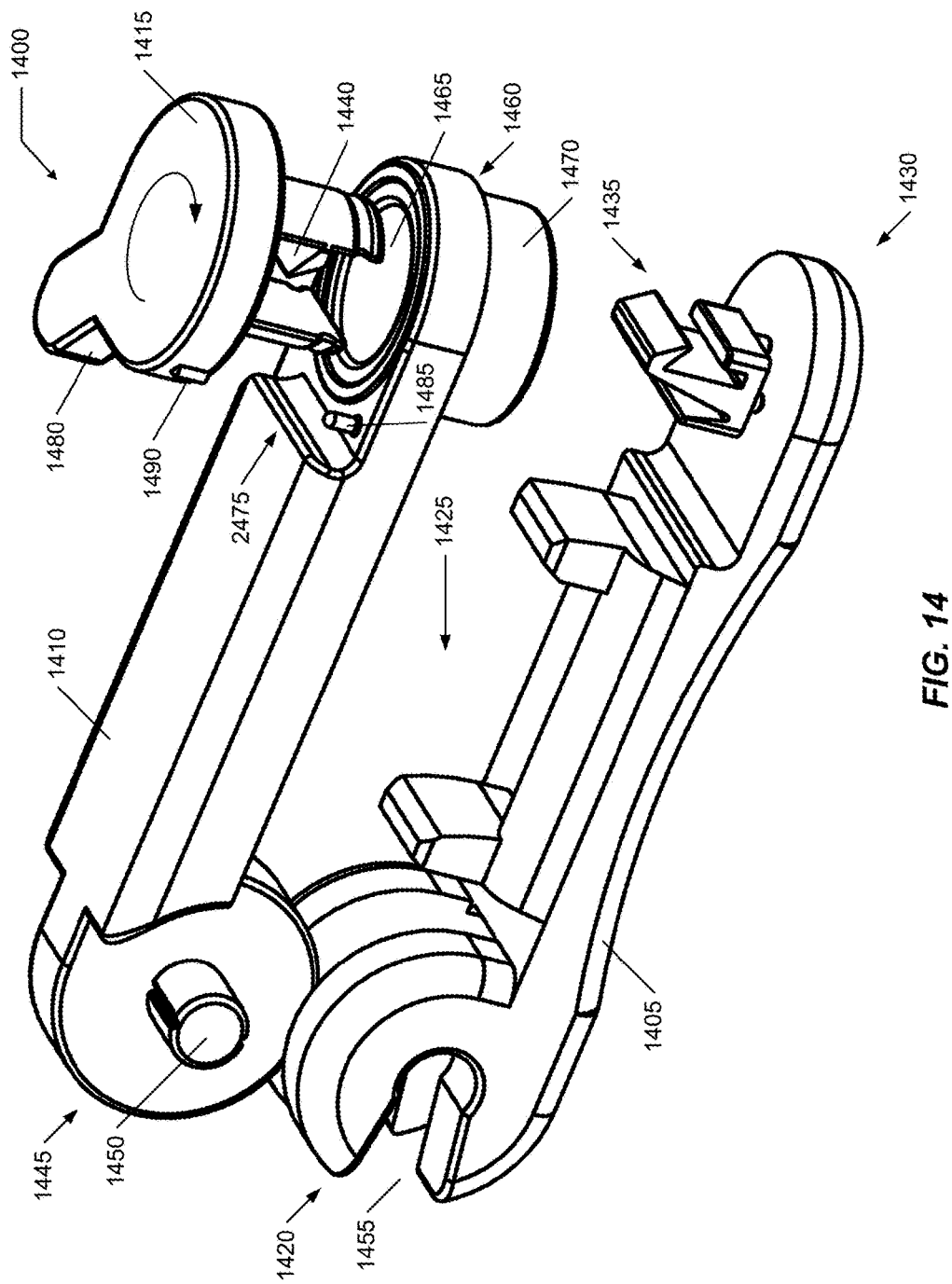
FIG. 14-FIG. 21 illustrate a second alternate embodiment for a catheter clamp.
Figure 15:
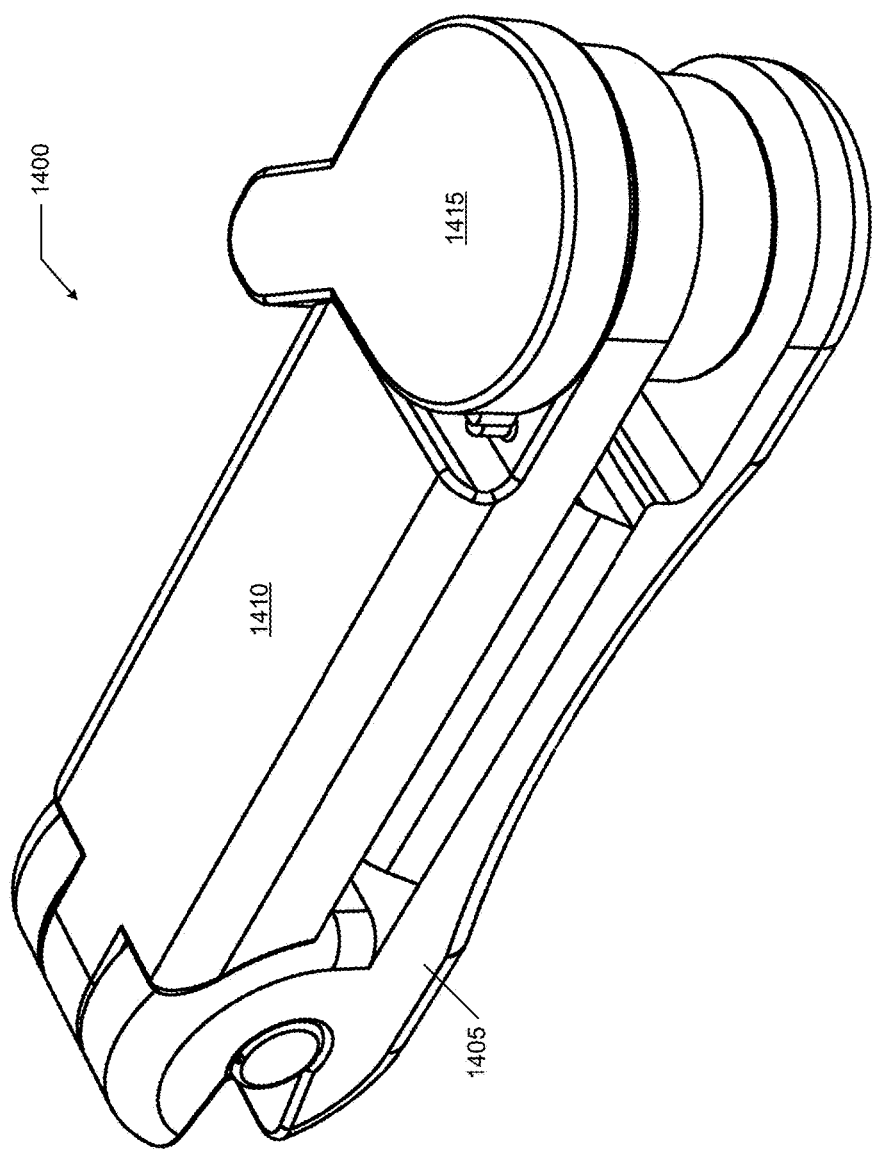
Figure 16:
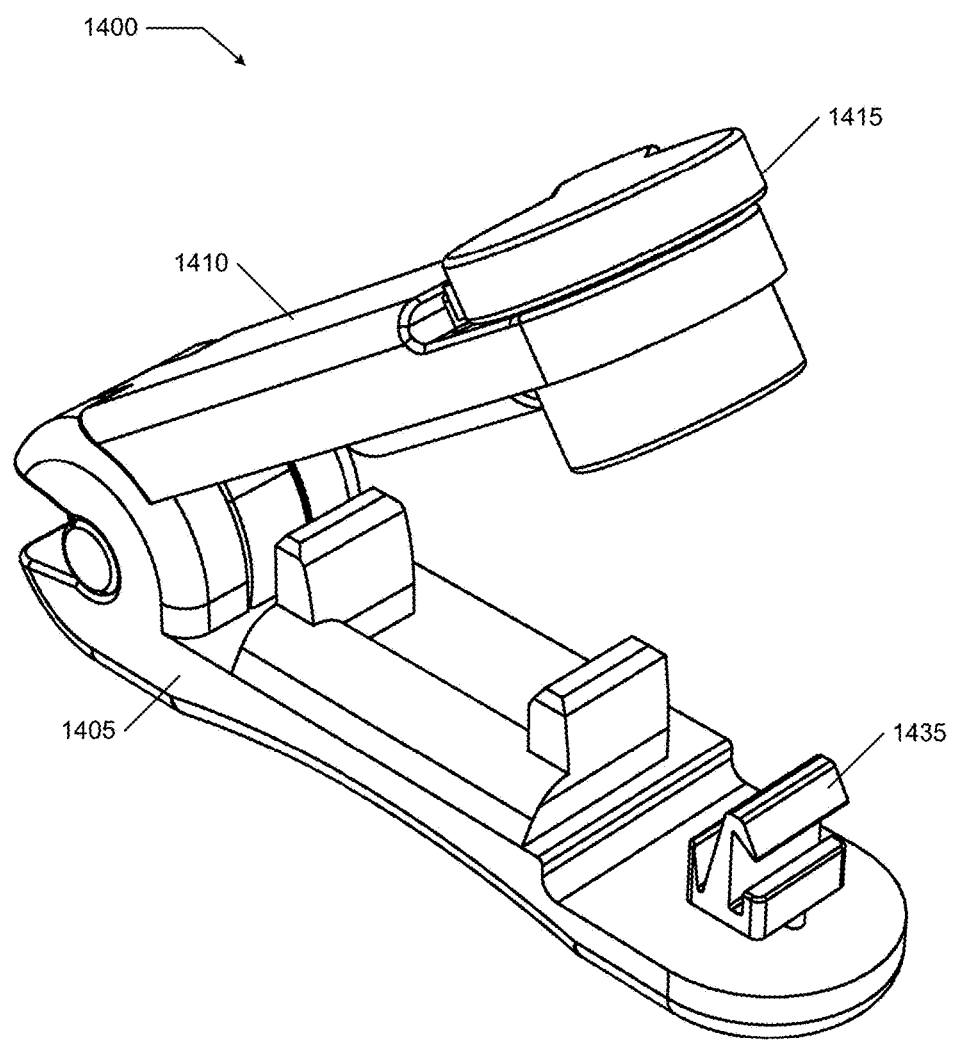
Figure 17:
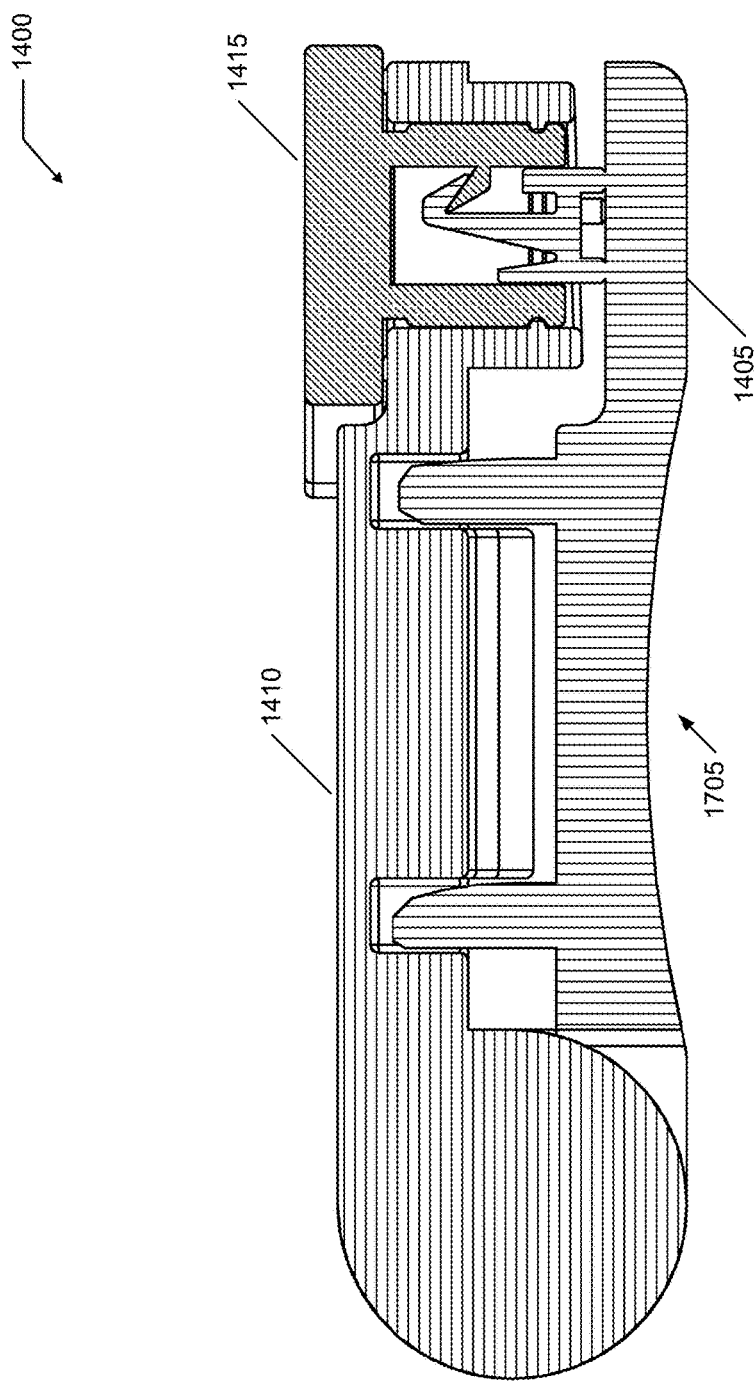
Figure 18:
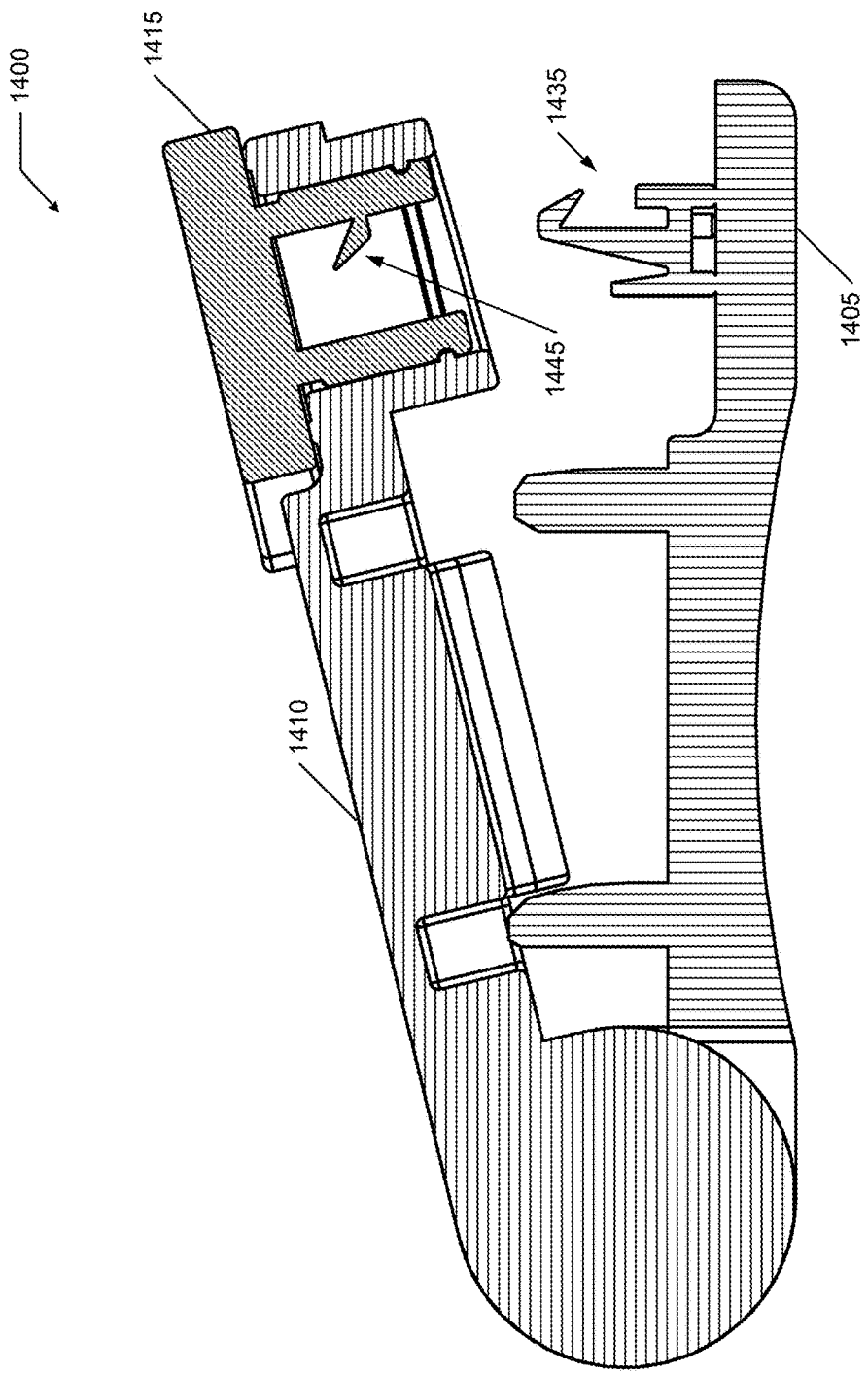
Figure 19:
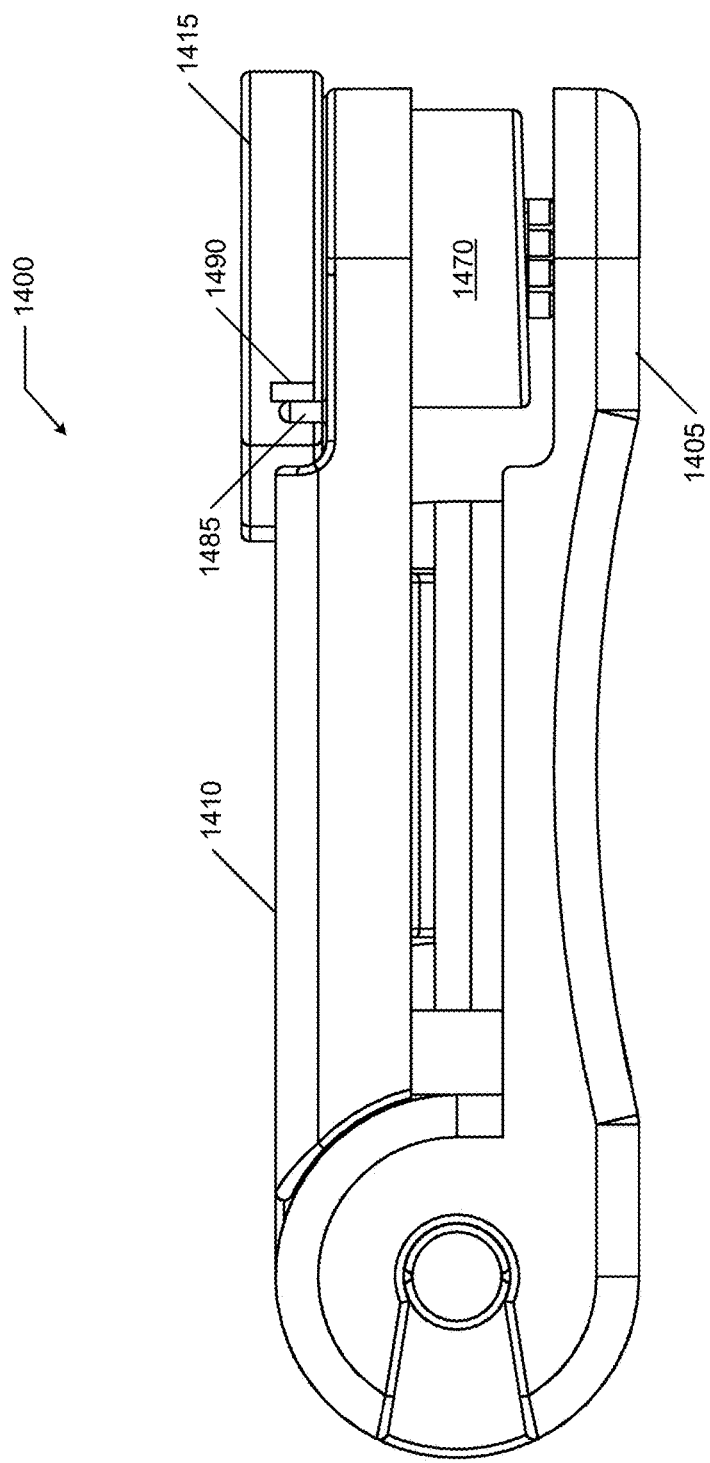
Figure 20:
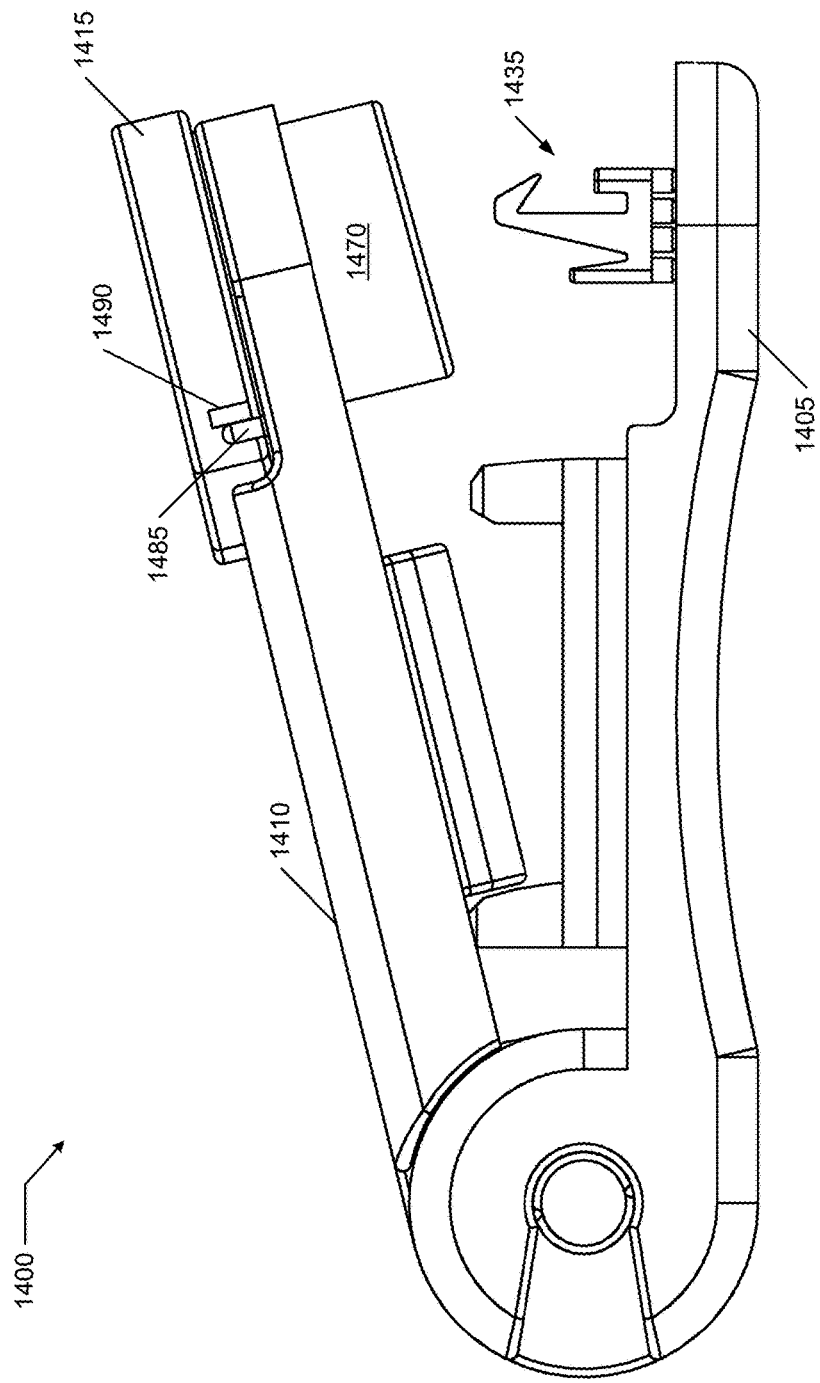

FIG. 14-FIG. 21 illustrate a second alternate embodiment for a catheter clamp 1400. FIG. 14 illustrates an exploded view of second alternate catheter clamp 1400, FIG. 15 illustrates an isometric view of second alternate catheter clamp 1400 in the closed mode, FIG. 16 illustrates an isometric view of second alternate catheter clamp 1400 in the open mode, FIG. 17 illustrates a section view of second alternate catheter clamp 1400 in the closed mode, FIG. 18 illustrates a section view of second alternate catheter clamp 1400 in the open mode, FIG. 19 illustrates a side view of second alternate catheter clamp 1400 in the closed mode, and FIG. 20 illustrates a side view of second alternate catheter clamp 1400 in the open mode.

Clamp 1400 includes three main components: a bottom arm 1405, a top arm 1410 moveably coupled to bottom arm 1405, and a knob 1415 moveably coupled to top arm 1410. The general idea is that top arm 1410 is pivotally coupled to a first end 1420 of bottom arm 1405 allowing top arm 1410 to open and close relative to bottom arm 1405. An engagement cradle system 1425, as disclosed and described in the previous embodiments, is disposed on inside engaging faces of the arms. When the arms are closed, cradle system 1425 is active and when the arms are opened, cradle system 1425 is inactive. Bottom arm 1405 includes a second end 1430 supporting a bottom latching element 1435. Knob 1415 includes a top latching element 1440 complementary to bottom latching element 1435. The latching elements are designed for single-use latching engagement (in some implementations may include a ratcheting configuration as well as described with respect to other embodiments). That is, once element 1440 engages element 1435, the latching system remains engaged unless and until the latching system is destroyed as further explained herein. Activation of the latching system occurs when top arm 1410 is closed relative to bottom arm 1405 which activates cradle system 1425. As long as the latching system is engaged and non-compromised, the arms are closed and cradle system 1425 is active.

Top arm 1410 includes a first end 1445 supporting an axle 1450. Axle 1450 is designed to slide into a complementary slot 1455 in first end 1420 when the arms are open. As long as the arms are closed, axle 1450 may not be removed from slot 1455. Once axle 1450 engages slot 1455, the arms may rotate about their first ends between the open and closed modes.

A second end 1460 of top arm 1410 includes an aperture 1465 for receiving knob 1415 and a protective shield 1470 limiting access to the hooks when the arms are in the closed mode. Knob 1415 rotates within aperture 1465 when the arms are closed and the latching system is engaged to tear away bottom latching element 1435 from second end 1430 and thereby destroy the latching system and enable the arms to return to the open mode and deactivate cradle system 1425. Clamp 1400 is thereby rendered inoperable and incapable of further use to latch into the closed mode. Protective shield 1470 inhibits manipulation of the latching elements while the arms are closed and the latching system is engaged. Allowing manipulation of the latching elements may permit a non-destructive opening of clamp 1400 and reducing an effectiveness of clamp 1400 as a tamper-resistant and tamper-evident closure system.

A general operation of clamp 1400 is similar to the other embodiments. Specific modifications include a number of changes for comfort, ease of operation, and safety. For example, introduction of a concavity 1705 in an outside surface of bottom arm 1405 provides additional comfort against a body surface of a user. In some cases, there may be a concern that a user may inadvertently activate the opening mechanism. For example, in an implementation in which an actuating arm extends significantly above a top surface of a top arm (see, for example, arm 940 of FIG. 9), there is a concern that a user may unintentionally snag the arm resulting in an accidental opening of the clamp. To reduce such concerns, top arm 1410 includes an indent 1475 at second end 1460. Knob 1415 is recessed into indent 1475 reducing an ability of accidental snagging by presenting a low profile above top arm 1410. Further, knob 1415 includes a small handle 1480 that abuts or is very close to a wall of indent 1475 when knob 1415 is in the locking position. The short length of handle 1480 further limits an ability to accidentally rotate knob 1415. To destroy the latching system, handle 1480 is used to rotate knob 1415 within aperture 1465 to separate bottom latching element 1435 from bottom arm 1405. An optional detent system resists such rotation and helps to ensure that any rotation of knob 1415 is purposeful.

The detent system may include a pair of obstructing protrusions, such as a post 1485 and an extension 1490 on an outer periphery of knob 1415. The resistive force of the detent system must be overcome to rotate knob 1415 sufficiently to tear away bottom latching element 1435 and allow for an opening of clamp 1400. A magnitude of the resistive force is variable based upon the materials used, size of the components of the detent system, and amount of engagement between the components, among other factors.

An additional feature of the latching system is that bottom latching element 1435 is retained within knob 1415 and engaged with top latching element 1440 after destruction. A feature of the latching system to help control how bottom latching element 1435 separates from bottom arm 1405 is to couple bottom latching element 1435 to bottom arm 1405 using a set of posts and stress risers between each post and bottom arm 1405. Clamp 1400 further includes a stress riser between top latching element 1440 and an inside surface of knob 1415 to help predictably control a secondary failure mode of the latching system which causes top latching element 1440 to separate from knob 1415. This secondary failure mode may occur in response to forcibly opening the arms without rotating knob 1415, for example.

Figure 21:
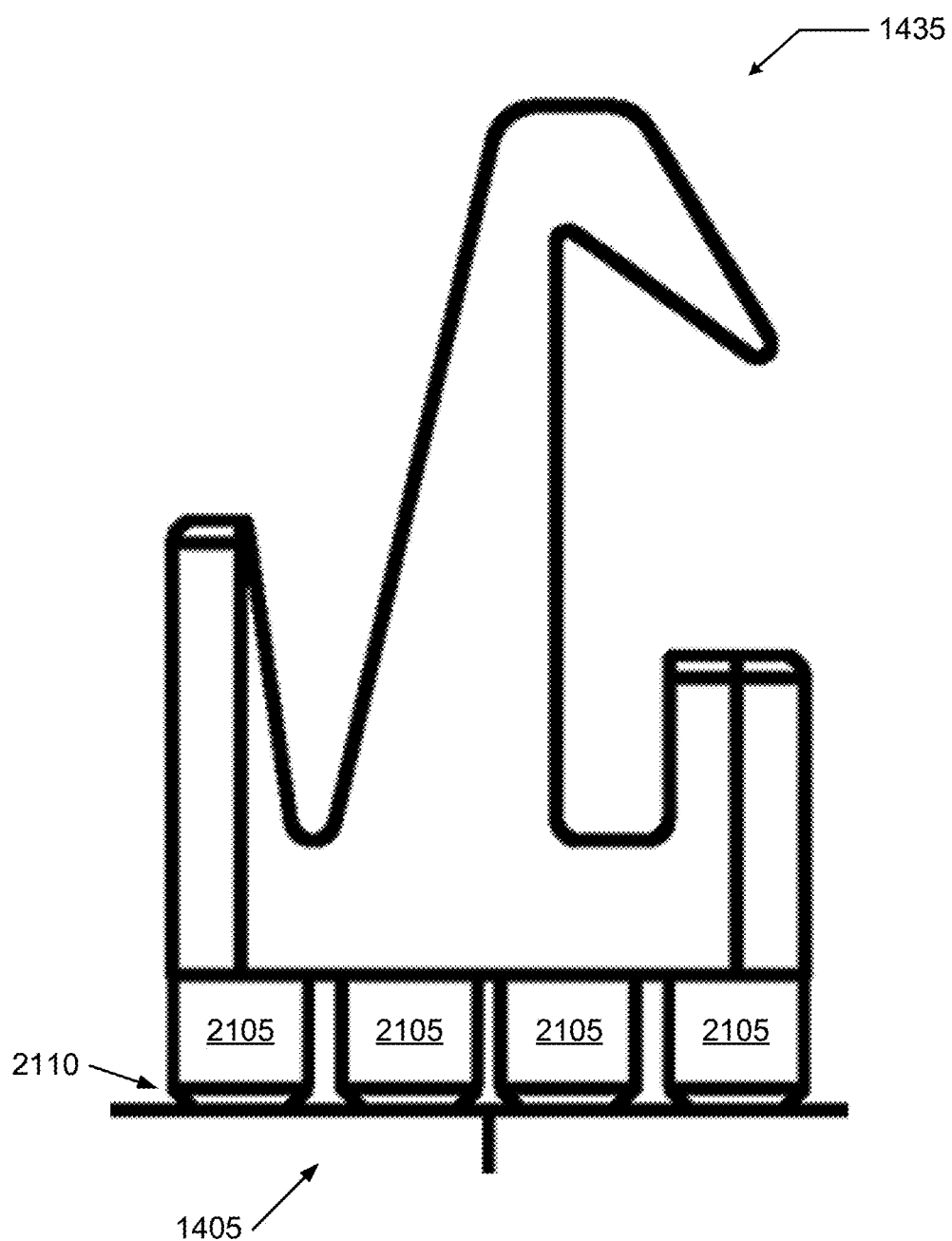

FIG. 21 illustrates a close-up detail of an attachment of bottom latching element 1435 to bottom arm 1410 using a set of posts 2105, each post 2105 having a stress riser 2110 attaching it to bottom arm 1405. A stress riser is a physical detail that causes a load on the body to focus on a specific area or location. That focus, in this case, directs the tearing/separation of posts 2105 from bottom arm 1405 at stress risers 1210 in response to rotation of knob 1415. Bottom latching element 1435, and a majority of the set of posts 2105 are retained within knob 1415 after separation.

Figure 22:
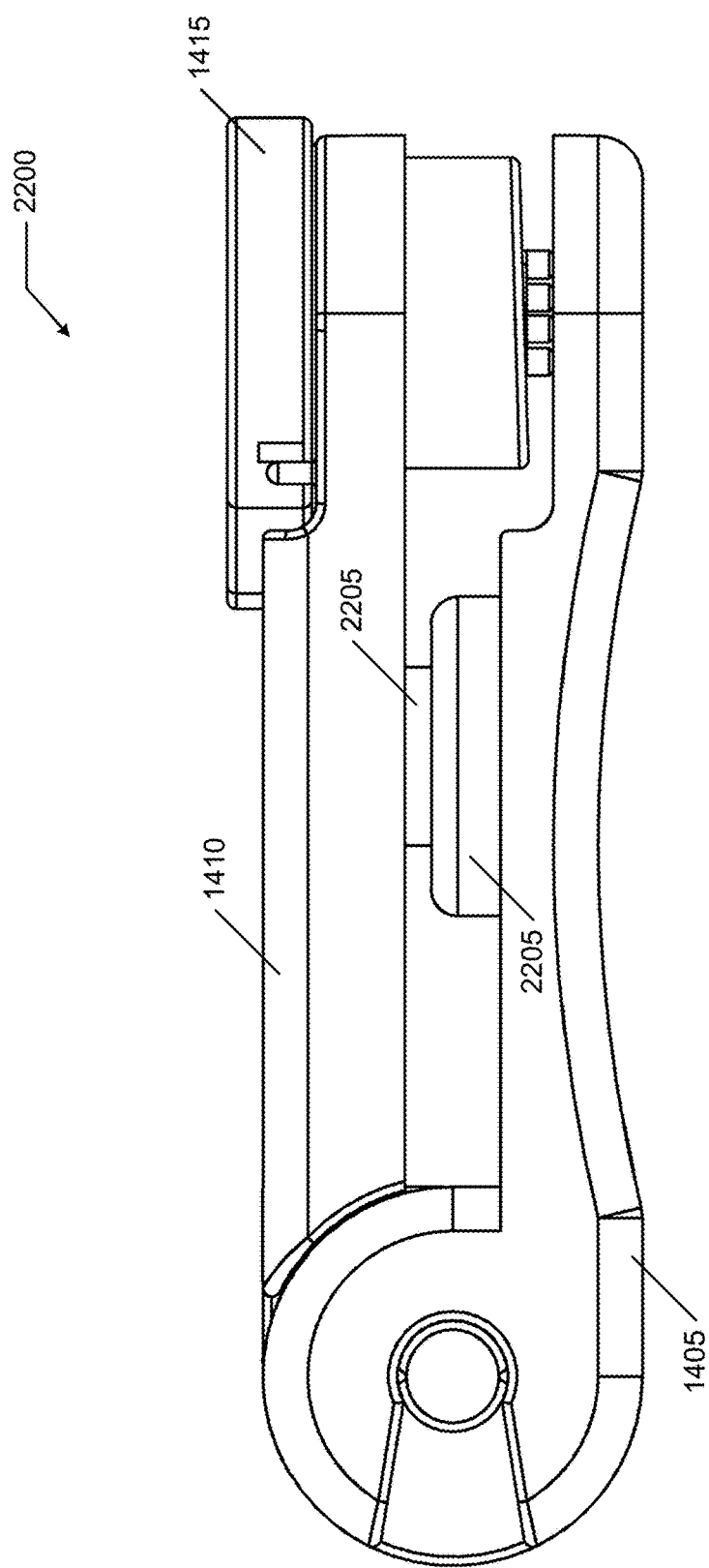
FIG. 22-FIG. 24 illustrate a modified embodiment for a generalized tamper-evident clamp.
Figure 23:
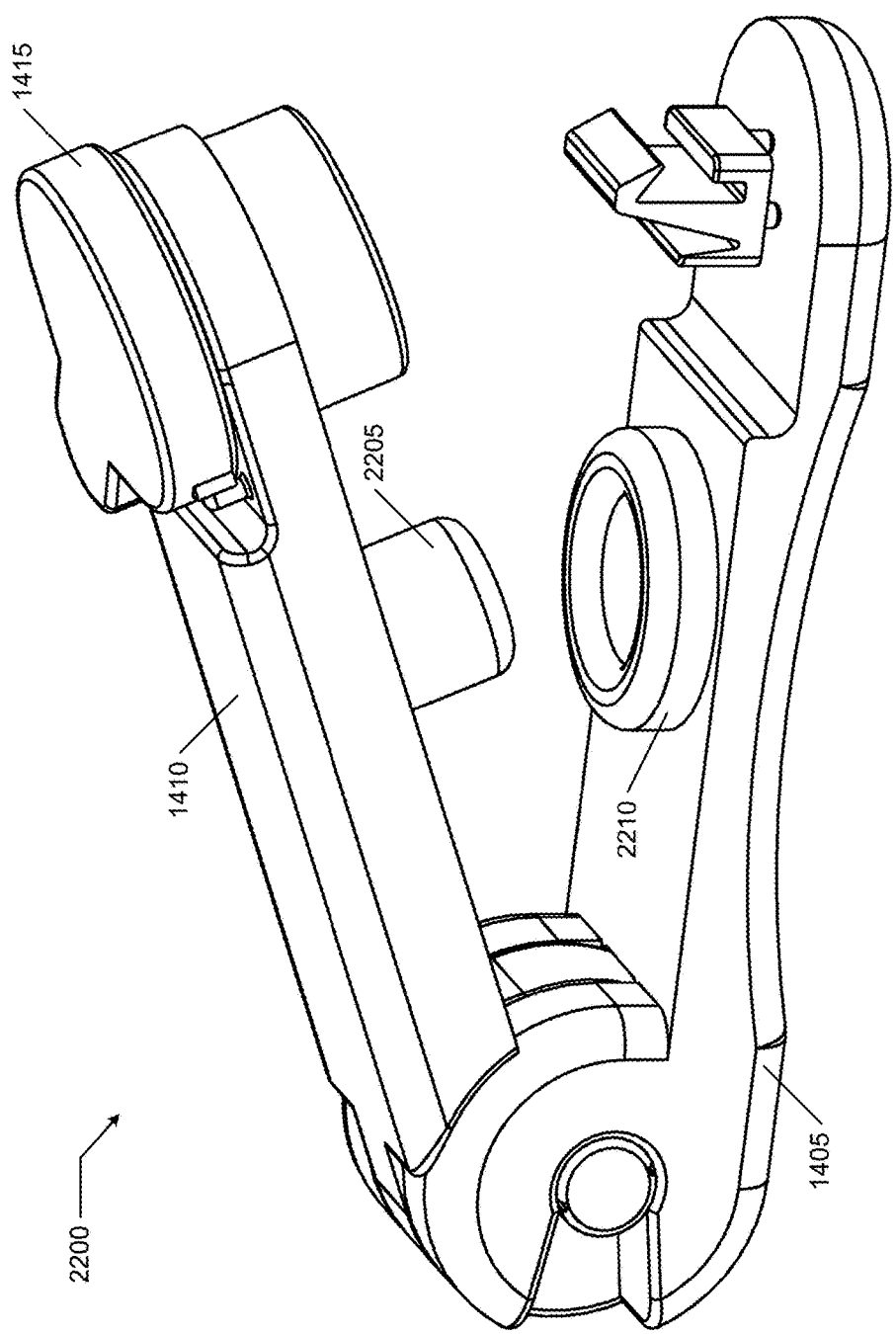
Figure 24:
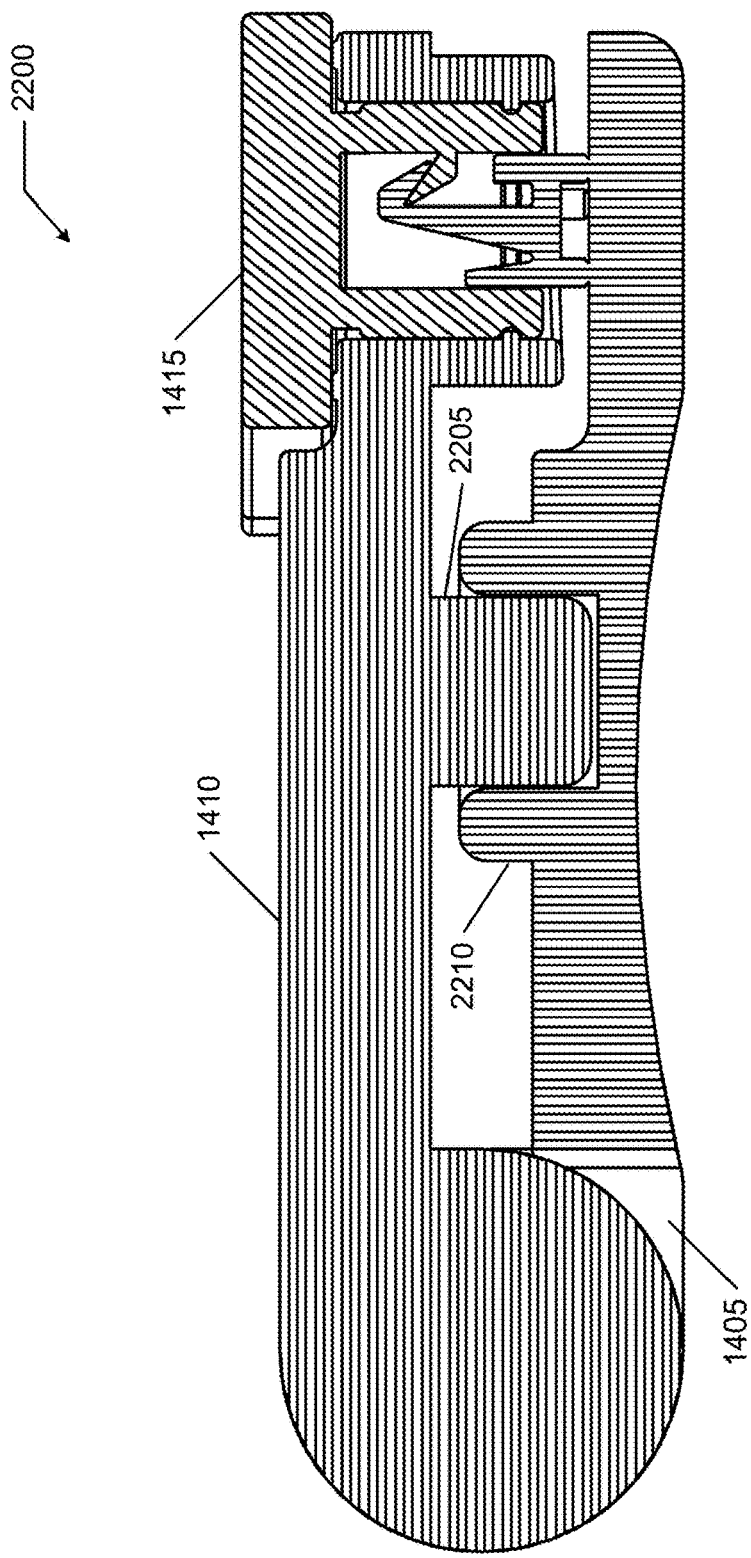

FIG. 22-FIG. 24 illustrate a modified embodiment for a generalized tamper-evident clamp 2200. FIG. 22 illustrates clamp 2200 in the closed mode, FIG. 23 illustrates clamp 2200 in the open mode; and FIG. 24 illustrates a sectional view of clamp 2200 in the closed mode. Clamp 2200 differs from other clamps illustrated in FIG. 1-FIG. 21 in that the catheter cradle system has been replaced by an interlocking pin 2205 that engages/locates into a hollow cylinder 2210. In other respects, clamp 2200 may be as described with respect to clamp 1400. Specifics of bottom arm 1405, top arm 1410, and knob 1415 may be adjusted for a particular application, but general functional principles are consistent with the description herein of the latching, tamper resistance, and tamper-evident features.

Clamp 2200 represents an application to uses beyond clamping and securing catheter lines. Pin 2205 and cylinder 2210 represent an alternative closure system controlled by the clamp mode (open or closed) which in turn is limited by a status of the latching system (intact or destroyed). Other implementations of clamp 2200 may employ different closure systems. Pin 2205 selectively engages cylinder 2210 when the arms are closed. The arms remain closed as long as the latching system is engaged and intact, which maintains the closure system closed. Clamp 2200 that has a destroyed latching system is evidence that the closure system may have been opened. The implications are dependent upon the application.

The potential applications are numerous. For example, the pin could go through a zipper and hook on an item of luggage so the user could know when their luggage had been tampered with. A utility company could use the clamp on energy meters to discourage customers from tampering with their meters. Or a concert venue could use the clamp to prove someone has paid to enter, a hospital could use for identification, instead of use of paper wrist bands that are difficult to remove without a tool that many patrons and patients find annoying. The closure system may be adapted for many different potential uses.

In some embodiments, it may be possible to restore functionality of a clamp by simply replacing a bottom arm having a new intact bottom latching element. In some cases, it may be desirable to replace both the bottom arm and knob. Reuse of one or more components may help to reduce an overall cost of the system. For example, an embodiment in which the primary delatchment strategy would be destruction of the top latching element within the knob, replacement of the knob may be all that is necessary to re-enable full functionality.

The system and methods above has been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. A clamp, comprising:
   a first arm defining a first component of a closure system;
   a second arm, hingedly coupled to said first arm, defining a second component of said closure system, said second component of said closure system complementary to said first component, said closure system having an access enabled mode and an access inhibited mode wherein said components are engaged when said closure system is in said access inhibited mode and wherein said components are disengaged when said closure system is in said access enabled mode; and
   a single-use tamper-evident locking system coupled to said first and second arms and configured to control said access enabled and said access inhibited modes of said closure system, said closure system retained in said access inhibited mode when said arms are closed relative to each other and said single-use tamper-evident locking system is active to retain said first and second arms in a closed mode wherein said single-use tamper-evident locking system is configured to destructively delatch before said first and second arms may be operated to an opened mode after an engagement of said single-use tamper evident locking system wherein said closure system may be returned to the access enabled mode;
   wherein said single-use tamper-evident locking system includes a bottom latching element disposed on an end of the first arm, wherein said single-use tamper-evident locking system further includes a knob rotatably coupled to an end of said second arm opposite of said end of said first arm, wherein said knob includes an internal cavity supporting a top latching element complementary to said bottom latching element, and wherein said top and bottom latching elements are engaged when said first and second arms are moved to said closed mode, thereby engaging said single-use tamper evident locking system.

2. The clamp of claim 1 wherein a rotation of said knob relative to said end of said second arm after said engagement detaches said bottom latching element from said end of said first arm.

3. The clamp of claim 2 wherein said closure system defines a catheter cradle, said catheter cradle including a first clamping surface disposed between a pair of extending sidewalls as part of said first component, wherein said catheter cradle includes a second clamping surface disposed between a pair of sidewall receiving apertures and longitudinally offset from said first clamping surface as part of said second component, and wherein said engagement proximates said first and second clamping surfaces and engages said pair of sidewalls within said pair of sidewall receiving apertures.

4. The clamp of claim 3 wherein a first particular arm of the first and second arms includes an axle element defining a hinging axis and wherein a second particular arm of the first and second arms couples to said axle element defining a hinging rotation about said hinging axis for a relative movement between said first and second arms.

5. The clamp of claim 4 wherein said knob rotates about a knob axis that is orthogonal to and offset from said hinging axis.

6. The clamp of claim 1 wherein said closure system defines a catheter cradle, said catheter cradle including a first clamping surface disposed between a pair of extending sidewalls as part of said first component, wherein said catheter cradle includes a second clamping surface disposed between a pair of sidewall receiving apertures and longitudinally offset from said first clamping surface as part of said second component, and wherein said engagement proximates said first and second clamping surfaces and engages said pair of sidewalls within said pair of sidewall receiving apertures.

7. The clamp of claim 6 wherein a first particular arm of the first and second arms includes an axle element defining a hinging axis and wherein a second particular arm of the first and second arms couples to said axle element defining a hinging rotation about said hinging axis for a relative movement between said first and second arms.

8. The clamp of claim 7 wherein said knob rotates about a knob axis that is orthogonal to and offset from said hinging axis.

\* \* \* \* \*